United States Patent
Musick et al.

(10) Patent No.: US 6,458,593 B1
(45) Date of Patent: Oct. 1, 2002

(54) IMMORTALIZED CELL LINES AND METHODS OF MAKING THE SAME

(75) Inventors: James R. Musick, Conifer; John Charles Gill, IV, Boulder; Bruce P. Burnett, Aurora; Tammy E. Hedlund, Morrison, all of CO (US)

(73) Assignee: Vitro Diagnostics, Inc., Littleton, CO (US)

( * ) Notice: Subject to any disclaimer, the term of this patent is extended or adjusted under 35 U.S.C. 154(b) by 0 days.

(21) Appl. No.: 09/489,085

(22) Filed: Jan. 21, 2000

Related U.S. Application Data

(60) Provisional application No. 60/116,814, filed on Jan. 21, 1999.

(51) Int. Cl.$^7$ .............................................. C12N 15/64
(52) U.S. Cl. ........................ 435/458; 435/467; 435/366
(58) Field of Search ................................ 435/458, 467, 435/366

(56) References Cited

U.S. PATENT DOCUMENTS 5,629,159 A    5/1997   Anderson ....................... 435/6

FOREIGN PATENT DOCUMENTS

| | | |
|---|---|---|
| FR | 2 681 609 | 9/1991 |
| WO | WO 98/56393 | 12/1998 |
| WO | WO 99/35245 | 7/1999 |
| WO | WO 99/37752 | 7/1999 |

OTHER PUBLICATIONS

Edelstein et al., *Diabetologia*, 41:736–739 (1998).
Falchetti et al., *Oncogene*, 18:1515–1519 (1999).
Offord et al., *Invest. Opthalmol. Vis. Sci.*, 40:1091–1101 (1999).
Prasad et al., *In Vitro Cell. Dev. Biol.*, 30A(9):596–603 (1994).
Raymon et al., *J. Neurosci.*, 19(13):5420–5428 (1999).
Stapleton et al., *Oncogene*, 6:807–818 (1991) (Abstract).
Ham et al., *J. Clin. Endocrinol.*, 83(5):1598–1603 (1998).

*Primary Examiner*—James Ketter
(74) *Attorney, Agent, or Firm*—Sheridan Ross P.C.

(57) ABSTRACT

The present invention relates to methods of immortalizing various primary cell cultures, including pituitary cells, neurons, beta islet cells, glial cells, corneal epithelial cells and follicular stellate cells. The primary cells are transfected with a vector containing an establishment oncogene, resulting in non-transformed immortalized cells. The primary cells and/or the subsequent immortalized cells are cultured in a defined media containing one or more environmental factor(s) that control the proliferation and/or differentiation of the cells.

38 Claims, 10 Drawing Sheets

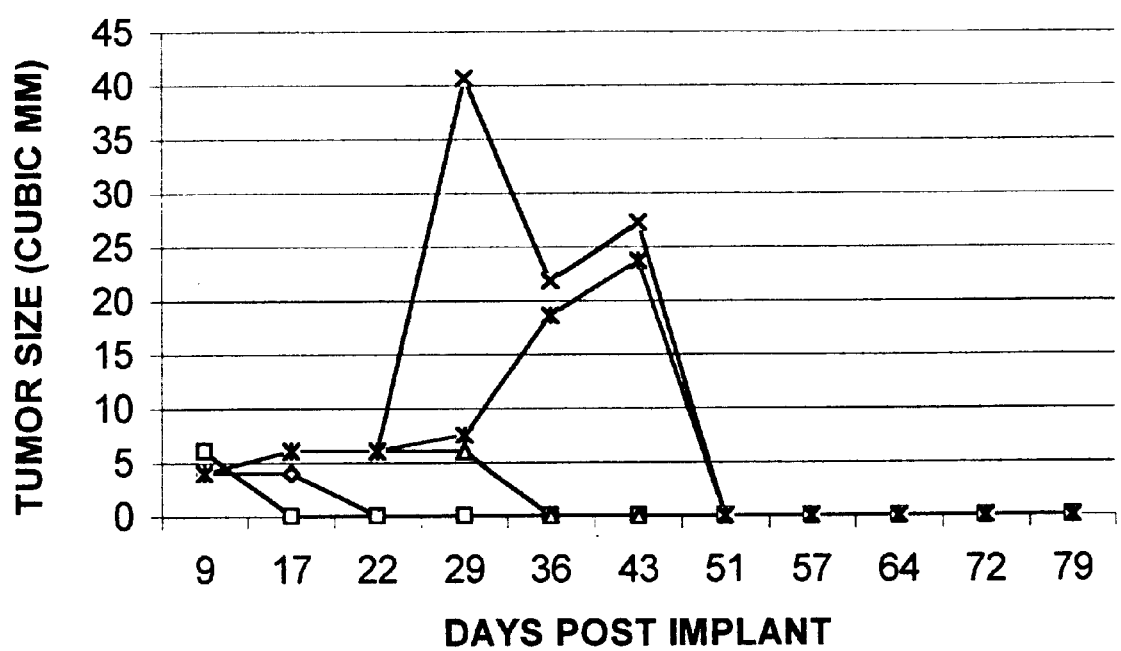

SEQUENCE LISTING

<160> NUMBER OF SEQ ID NOS: 10

<210> SEQ ID NO 1
<211> LENGTH: 35
<212> TYPE: DNA
<213> ORGANISM: Artificial sequence
<220> FEATURE:
<221> NAME/KEY: misc_feature
<222> LOCATION: (1)..(35)
<223> OTHER INFORMATION: primer

<400> SEQUENCE: 1
cgagcggaat tcgccatggt gcacggccag gcagc         35

<210> SEQ ID NO 2
<211> LENGTH: 39
<212> TYPE: DNA
<213> ORGANISM: Artificial sequence
<220> FEATURE:
<221> NAME/KEY: misc_feature
<222> LOCATION: (1)..(39)
<223> OTHER INFORMATION: primer

<400> SEQUENCE: 2
cgagcgggat ccctatgcac gagagttcct tagctgctc         39

<210> SEQ ID NO 3
<211> LENGTH: 34
<212> TYPE: DNA
<213> ORGANISM: Artificial sequence
<220> FEATURE:

```
<221> NAME/KEY: misc_feature
<222> LOCATION: (1)..(34)
<223> OTHER INFORMATION: primer

<400> SEQUENCE: 3
cgagcgaagc ttgccatggt gcacggcagg cagc                          34

<210> SEQ ID NO 4
<211> LENGTH: 39
<212> TYPE: DNA
<213> ORGANISM: Artificial sequence
<220> FEATURE:
<221> NAME/KEY: misc_feature
<222> LOCATION: (1)..(39)
<223> OTHER INFORMATION: primer

<400> SEQUENCE: 4
cgagcgaggc ctctatgcac gagagttcct tagctgctc                     39

<210> SEQ ID NO 5
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: primer

<400> SEQUENCE: 5
gcagctaatg gaccttctag gtc                                      23

<210> SEQ ID NO 6
<211> LENGTH: 23
<212> TYPE: DNA
<213> ORGANISM: Artificial sequence
<220> FEATURE:
<221> NAME/KEY: misc_feature
<222> LOCATION: (1)..(23)
<223> OTHER INFORMATION: primer

<400> SEQUENCE: 6
gtcagcagta gcctcatcat cac                                      23

<210> SEQ ID NO 7
<211> LENGTH: 24
<212> TYPE: DNA
<213> ORGANISM: Artificial sequence
<220> FEATURE:
<221> NAME/KEY: misc_feature
<222> LOCATION: (1)..(24)
<223> OTHER INFORMATION: primer

<400> SEQUENCE: 7
gcagctatct ttctggtcac attg                                     24

<210> SEQ ID NO 8
<211> LENGTH: 15
<212> TYPE: DNA
<213> ORGANISM: Artificial sequence
<220> FEATURE:
<221> NAME/KEY: misc_feature
<222> LOCATION: (1)..(15)
<223> OTHER INFORMATION: primer

<400> SEQUENCE: 8
gtggcacgcc gtgtg                                               15
```

-continued

```
<210> SEQ ID NO 9
<211> LENGTH: 18
<212> TYPE: DNA
<213> ORGANISM: Artificial sequence
<220> FEATURE:
<221> NAME/KEY: misc_feature
<222> LOCATION: (1)..(18)
<223> OTHER INFORMATION: primer

<400> SEQUENCE: 9
ctggcttcaa gagggcag                                                    18

<210> SEQ ID NO 10
<211> LENGTH: 21
<212> TYPE: DNA
<213> ORGANISM: Artificial sequence
<220> FEATURE:
<221> NAME/KEY: misc_feature
<222> LOCATION: (1)..(21)
<223> OTHER INFORMATION: primer

<400> SEQUENCE: 10
cgtagttctt gagcagtgcg t                                                21
```

IMMORTALIZED CELL LINES AND METHODS OF MAKING THE SAME

CROSS REFERENCE TO RELATED APPLICATIONS

This application claims the benefit of priority under 35 U.S.C. §119(e) from U.S. Provisional Application Ser. No. 60/116,814, filed Jan. 21, 1999, entitled "Immortalization of Pituitary Cells". The entire disclosure of U.S. Provisional Application Ser. No. 60/116,814 is incorporated herein by reference.

FIELD OF THE INVENTION

The present invention relates to methods of immortalizing primary cells and to the immortalized cell lines produced by these methods.

BACKGROUND OF THE INVENTION

The desirability of generating immortalized cell lines for use as in vitro models of various tissues has long been recognized. For example, researchers have endeavored for some time to generate a suitable in vitro model for cells of the anterior pituitary gland. The anterior pituitary gland of mammals is composed of specialized cells known to synthesize and secrete a variety of hormones that regulate critical body functions. Corticotropes express adrenocorticotropic hormone (ACTH) which regulates the steroid hormone output from the adrenal gland. Gonadotropes express the gonadotropin hormones, luteinizing hormone (LH) and follicle-stimulating hormone (FSH), which operate in concert to control reproductive functions. Thyrotropes are the source of thyroid-stimulating hormone (TSH), which regulates the synthesis and release of thyroid hormones from the thyroid gland. Somatotropes express growth hormone (GH), which controls cell growth. Lactotropes express a hormone closely related to growth hormone, prolactin which controls lactation and other functions as well. Prolactin was discovered in 1970 and its entire functional role is not yet understood (Hodson, Calif., 1996). Melanotropes express melanocyte-stimulating hormone (MSH), which regulates pigmentation of the skin. The suffix "troph" may be substituted for "trope" when referring to these cells. Control of end-organs regulated by anterior pituitary hormones is closely regulated by circulating end-organ hormones and neural inputs which interact at pituitary and hypothalamic sites to maintain homeostasis.

Some pituitary cell lines presently exist but these are usually neoplastic cells which continue to divide in vitro by virtue of malignant transformation, e.g., the GH-3 rat cell line was derived from a pituitary tumor. GH-3 cells are termed somatomammotrophs because they synthesize and secrete both prolactin and growth hormone. Other rat pituitary hormone-secreting cell lines are also known, e.g., GH-1, which was derived from the same tumor as the GH-3 line. The RC-4B/C cell line is an apparent mix of corticotropes, thyrotropes, lactotropes and somatotropes. Likewise, with regard to human pituitary cell lines, most of these come from neoplasms of the pituitary. Prolactinoma is the most prevalent form of pituitary neoplasm in man. Therefore, human lactotrope adenoma cells have been extensively studied to determine the genetic mechanisms of tumor formation; such studies suggest that expression of the hst gene encoding fibroblast growth factor may be associated with pituitary tumorigenesis (Cai, W Y, et.al., 1994; Gonsky, R et.al., 1991). Hydridomas formed by fusion of malignant cells with gonadotropes have been used to express human FSH (U.S. Pat. No. 4,383,034). LH has also been produced by fusion of human pituitary adenoma cells with a human lymphoblastoid cell line (U.S. Pat. No. 4,383,035).

Transformed cells are not the same as non-transformed cells present in the body. Transformation shifts the expression of endogenous proteins significantly, turning off the expression of some proteins, while the expression of other proteins is increased. Transformation also alters morphological and cellular properties, e.g. transformed cells require lower amounts of serum and growth factors to support proliferation. Transformed cells may also erroneously process proteins resulting in molecular alteration of endogenous proteins. Human cytomegalovirus immediate-early promoter was more efficient in directing reporter gene expression when expressed in transformed than non-transformed rat anterior pituitary cells suggesting that transformation alters transcriptional factors (Coleman, T A, et.al., 1991). Thus, a transformed pituitary cell may not reflect the normal physiological and cellular processes of its progeny.

Hormone-secreting cells of the pituitary can be grown in vitro as a primary culture. Such primary cultures of pituitary cells have been used extensively to investigate physiological processes involved in regulation of hormone secretion. For example, these cultures were used to bioassay specific hypothalamic releasing hormones that regulate hormone output of the pituitary. This discovery provided considerable insights into the mechanisms of intercommunications between the nervous and endocrine systems (Guillemin, 1978). However, after several cell divisions primary cultures invariably reach a crisis stage and thereafter cease to divide. This property is referred to as senescence. There are some pituitary cell lines which continue to proliferate in culture, but are apparently non-transformed. Mouse thyrotrope tumors such as TtT 97 result from thyroidectomy, synthesize and release TSH, and respond to T3 and TRH (Furth, J, 1955; Condliff, P G, et.al., 1969; Cacicedo, L, et.al., 1981). The rat somatomammotroph cell line, rPCO and clonal derivatives, was derived from primary culture of rat pituitary cells in media containing T3 and GHRH, which may have resulted in selective proliferation of somatotropes. RPCO cells synthesize and release growth hormone and prolactin; secretion is differentially affected by TRH, T3 and GHRH (Chomczynski, P, et.al., 1988; Kashio, Y, et.al., 1990). Both of these cell lines have been used in basic research into the molecular biology of pituitary hormone processing (Coleman, T A, et.al., 1991; Wood, W M, et.al., 1989). The mechanisms by which these cells are immortalized is unknown. These cells have not yet been definitively demonstrated to be non-transformed (Chomczynski, P, et.al., 1988).

Recombinant DNA technology has also been used to produce protein hormones of the pituitary gland. The non-glycosylated monomers of growth hormone and prolactin were initially expressed in *E. coli* cells using a recombinant plasmid containing the cDNA for growth hormone or prolactin. Recombinant protein accumulates in inclusion bodies primarily as reduced monomers. Following solubilization with urea, reoxidized monomers were recovered through use of reoxidation procedures which resulted in biologically active material similar to native hormones with the addition of a methionine residue at the amino terminus (Paris, N, et.al., 1990). The group of heterodimeric glycoprotein hormones including hCG, LH, FSH and TSH have also been expressed in Chinese Hamster Ovarian (CHO) cells using cloned sequences of both the homologous α-subunit and the hormone-specific β-subunit (Reddy, V B, et.al., 1985; Simon, J A, et.al., 1988; Keen, J L, et.al., 1989; U.S. Pat. No.

4,923,805; U.S. Pat. No. 5,156,957; U.S. Pat. No. 4,840, 896). These heterodimeric proteins are known to be glycoproteins containing 15%–35% carbohydrate as N-linked and O-linked glycans present on both the α and β-subunits. These carbohydrates add structural complexity and have various functions in the assembly, stabilization, modulation of biological activity and control of clearance of these molecules (Szkudkinski, M W, et.al., 1996; Galway, A B, et.al., 1990). The addition of carbohydrate moieties to the protein backbone is a function of the host cell and since these are different from the natural hormone-producing cells, variation in the glycosylation of recombinant hormones may result. Detailed comparison of urinary and recombinant human FSH (rhFSH) has shown that rhFSH is more acidic, suggesting differences in sialic acid content or terminal monosaccharides (de Leeuw, R, et.al., 1996). Also, recombinant human TSH (rhTSH) contains only sialic acid at terminal biantennary monosaccharides while pituitary-derived hTSH also contains sulfated N-acetyl galactosamine terminal residues. This results from the lack of N-acetyl galactosamine transferase in CHO cells used for the expression of rhTSH (Szkudlinski, M W, et.al., 1996).

There are non-transformed cells in the art which are thought to arise through spontaneous immortalization as occurs in non-malignant or benign tumors. However, these cell lines are relatively rare. Some other cells are known to undergo spontaneous immortalization without transformation. Studies of such cells showed that c-myc was over expressed while expression of other establishment oncogenes was unaltered, possibly due to a chromosomal translocation (Tavassoli & Shall, 1988; Madsen, et.al., 1992). Transfection of the v-myc oncogene into a murine macrophage cell line resulted in immortalization, suggesting that over expression of the myc oncogene itself was sufficient to induce immortality. Furthermore, the biological properties of the immortalized cell line were similar to normal cells (Blasi, et al., 1987). A variety of other studies have also demonstrated the immortalization effect of v-myc transfection into several different types of cells, including those with secretory functions common to endocrine cells (Strom, et.al., 1991; Bernard, et.al., 1989; Briers, et.al., 1993; Vanderstichele, et.al., 1994; Briers et.al., 1994; Hoeben, et.al., 1995).

Expression of the cellular myc gene is normally repressed by Lef/Tcf transcription factors which bind to specific sequences of the c-myc promoter (He, T C, et.al., 1998). In some forms of cancer and normal development, c-myc expression is increased through disruption of the developmental pathway known in the art as Wnt. The adenomatous polyposis coli gene (APC) is a tumor suppressor gene that is mutated in about 85% of all human colon cancers. The APC gene product is a component of the Wnt pathway that normally complexes β-catenin, preventing its effect on the nucleus. Mutations of the APC gene or activation of the Wnt pathway via ligand-receptor interaction result in disruption of the APC-β-catenin complex allowing β-catenin access to the nucleus. β-catenin then binds to Tcf transcription factors, de-represses the c-myc gene resulting in its increased transcription (He, TC, et.al., 1998; Dale, 1998). Increased cell proliferation in response to developmental signals and in colon cancer is mediated by increased c-myc expression.

The protein product of the myc gene is a transcription factor which forms a heterodimeric complex with another protein, Max. Myc is a central regulator of cell proliferation through transcription effects, including repression and activation of target gene expression, e.g., MrDd and cdc25A (George, K H; 1996). The latter target also induces apoptosis in cells. Max also forms homodimers and heterodimers with Mad and Mxi-1, alternative partners to Myc, which compete with Myc/Max for common gene targets. These various interactions are thought to regulate the ultimate effect of Myc over expression, i.e., cell differentiation, immortalization without transformation, transformation, or cell death (Facchini, L M and Penn, L Z; 1998; Desbarats, L, et.al., 1996; Amati, B and Land, H; 1994).

The SV40 virus has been used to immortalize several cells of animal and human origin. The pSV3neo plasmid containing the complete SV40 early genetic region including the large T and small T antigens was used to immortalize rat Leydig cells (Nagpal, M L, et.al., 1994). Two cell lines resulted which were maintained for 35 passages without apparent transformation as indicated by an absence of the anchorage-independent growth in soft agar. The large T antigen coding sequence had become integrated into the cellular genome. These cells displayed many characteristics of differentiated Leydig cells including expression of LH receptors (LH-R), insulin-like growth factor I (IGF-I) and IGF-I receptors (IGF-IR) and IGF binding protein 2 (IGFBP-2). The amounts of transcripts of the LH-R gene were lower, IGF-I, IGF-IR were the same and IGFBP-2 were much higher in the immortalized cells. Also, the immortalized cells could not synthesize testosterone due to low levels of the enzyme P450scc. Hence, the immortalized cells maintained some, but not all, differentiated characteristics of rat Leydig cells (Nagpal, M L, et.al., 1994). In order to avoid production of virus particles in permissive and semipermissive cells, including human and monkey cells, SV40 plasmids containing the large T antigen gene were modified to block viral replication by deleting part of the viral origin of replication, the so-called orin SV40 mutant (Gluzman, 1980). Such mutants have been particularly valuable in the immortalization of human cells (Chow, J Y, 1989), including granulosa cells, fetal liver epithelial cells, breast and other epithelial cells (Byong-Lyul, L, et.al., 1996; Ishida, T, et.al., 1995; Berthon, et.al., 1992; Lechner, M S and Laimins, L A, 1991). Human cell lines immortalized by SV40 Large T antigen exhibit increased growth in culture. However, they usually reach secondary senescence and are no longer viable (Stein, G H, 1985).

The degree of differentiation of the cells depends on the status of differentiation at the time of transfection. Thus, fetal liver cells immortalized by the plasmid pMK16-SV40 (ori⁻) failed to express α-fetoprotein (AFP) possibly because it had not yet differentiated at the time of establishment of the cell line (Ishida, T, et.al., 1995). The SV40 large T antigen is thought to combine with the products of the tumor suppressor genes p53 and p105-Rb, neutralize anti-oncogenic effects of these genes, including activation of apoptosis and thereby increase cell proliferation. Such effects may also lead to malignant transformation. Two immortalized breast epithelial cell lines resulted from transfection by the SV40 large T antigen. One of these lines remained non-transformed while another resulted in a transformed cell line, showing that SV40 large T antigen can result in immortalization and malignant transformation (Berthon, P, et.al., 1992).

The temperature sensitive mutant of SV40 large T (tsA58) has also been used to immortalize cells, including human pituitary thyrotropes. At the permissive temperature, the large T antigen is expressed and cells exhibit a transformed phenotype. At the non-permissive temperature, large T antigen is no longer expressed and cells revert to the normal differentiated phenotype (Chou, J Y, 1989). Adult human thyrotropes transfected with tsA58 plasmid proliferated at the permissive temperature 33° C. and showed no growth at 39° C. These cells have undergone more than 150 passages. Contrary to adult thyrotropes, these immortalized thyrotropes did not express TRH receptors nor do these cells secrete hTSH (Ham, et.al., 1998). The large T antigen of SV40 has also been used to immortalize specific pituitary tumor cells at discrete stages of development by constructing large T antigen-containing transgenes driven by various promoters that are differentially activated during development (Windle, J J, et.al., 1990; Alarid, E T, et.al., 1996). A hybrid of the adenovirus-12 and the SV40 virus has also been used to immortalize human prostate cells. These cells express many of the normal phenotypic characteristics of human prostate cells and were non-tumorigenic (U.S. Pat. No. 5,610,043).

Accordingly, a need exists for methods of immortalizing primary cultures of various cell lines that are not transformed. The present invention satisfies this need and provides related advantages.

SUMMARY OF THE INVENTION

The present invention relates to novel methods for the generation of immortalized cell lines from primary cultured cells and to such immortalized cell lines. Such cell lines are immortalized lines derived, for example, from hormone-producing cells of the pituitary gland, i.e., lactotropes, somatotropes, thyrotropes, gonadotropes, corticotropes or melanotropes. Supporting cells normally associated with endocrine cells such as follicular stellate cells may also be immortalized as described herein as well as neurons, glial cells, corneal epithelial cells, and β-islet cells of the pancreas which produce insulin.

Such cell lines are immortalized but not transformed as occurs during malignant transformation of a normal cell into a cancerous cell. Hence the immortalization of these cells is not secondary to malignant transformation.

Furthermore, the cells of a given line are maintained in culture under conditions allowing expression of the adult phenotype of the cell. For pituitary cells, the adult phenotype includes properties such as: presence of the appropriate hormone and secretory ultrastructure, secretion of such hormone in response to those secretagogues which normally regulate hormone secretion in the adult organism, receptors for the hypothalamic releasing hormone normally present on adult cells, expression of hormone-encoding genes, and expression of appropriate differentiation factors such as, for example, Pit-1 or SF-1 (Simmons, D M, et.al., 1990; Sanno, N, et.al., 1998; Bedford, et.al., 1996).

The present invention also refers to immortalization of cells from different species. Thus primary cells immortalized according to the present invention may be derived from various species, including for example, human, equine, bovine, canine, rat or mouse.

A feature of the present invention is that it involves use of both environmental factors and genetic manipulation of primary cultured cells to achieve or maintain immortalization without transformation at the fully differentiated phenotype. Environmental factors, such as the osmolarity of the cell culture media, addition of various growth factors and tissue extracts have been used to extend the longevity of cultured pituitary cells (e.g., U.S. Pat. Nos. 4,124,448 & 5,747,341). Significant effects of environmental factors on primary culture of pituitary cells, including effects on differentiation and proliferation have also been observed. In one embodiment, the present invention involves use of environmental factors to induce specific states of differentiation and/or proliferation prior to use of establishment oncogenes including, for example, the large T antigen of the SV40 virus and controlled expression of the myc proto-oncogene to immortalize cells. In another embodiment, specific environmental conditions can be used to maintain immortalized cell cultures that already possess desired properties such as a particular state of differentiation, hormone expression or proliferation without the need to induce such states. Furthermore, environmental conditions may also be used to control the expression and differentiation of cells that have been immortalized according to the methods of the present invention.

The present invention offers significant advantages over the prior art. This invention provides an alternative source of relatively pure native protein hormones for various applications in research, diagnostics and therapeutics. Presently, native material is derived through the extraction of tissues and the purification of each hormone present within such tissue. The physical and chemical properties of some hormones are closely related, for example pituitary growth hormone and prolactin are structurally similar. Prolactin is thought to have evolved from growth hormone (Cooke, N E, et.al., 1981). Thus, complete elimination of one hormone from the other is difficult; usually, purified hormone is at least partially contaminated with the other.

The present invention provides for cultures of pure hormone-producing cells without contamination by cells which produce other hormones. Thus, for example, this invention allows a pure culture of immortalized lactotropes without somatotropes. Likewise a clonal culture of pure somatotropes is possible without the presence of lactotropes. Hence, cultures of immortalized lactotropes provide a crude prolactin sample devoid of contamination by growth hormone and somatotrope cultures provide crude growth hormone uncontaminated by prolactin. Optimization of the secretion of the desired pituitary hormone provides additional advantages in purification to homogeneity as the hormone content in the culture media may be enriched, while other contaminating proteins are minimized. Purification methods well-known in the art (Sinha, Y N) may then be applied to culture media enriched by the secretion of, for example, prolactin or growth hormone exclusively to generate highly purified material uncontaminated by related hormones. Absolute purity of hormones is desirable in such applications as hormone structure-function determinations and therapeutic uses of these hormones. Gonadotropes are known to produce both LH and FSH. Hence, gonadotrope cultures do not provide sources of impure hormone devoid of gonadotropin contamination.

Another advantage of the present invention in its use as an alternative source for native pituitary hormones concerns the state of glycosylation of the heterodimeric glycoprotein hormones LH, FSH and TSH. Glycans are added post-translationally to the polypeptide chains composing the alpha and beta subunits. Glycosylation is a property of the cell expressing the hormone. As previously noted, rhTSH contains only sialic acid at terminal biantennary monosaccharides while pituitary-derived hTSH also contains sulfated N-acetyl galactosamine terminal residues resulting from the lack of N-acetyl galactosamine transferase in CHO cells used for the expression of rhTSH (Szkudlinski, M W, et.al., 1996). Since the present invention utilizes the endogenous cell from which native hormone arises, such a source can provide glycosylation patterns closer to native hormones than heterologous cells. The structure of the carbohydrate containing moieties contained in pituitary hormones is known to be an important determinant of function. A study comparing pituitary-derived human FSH, rhFSH, chemically deglycosylated FSH, and FSH expressed in a baculovirus expression vector/Sf9 cell system which fails to glycosylate FSH found substantial loss of biological activity in the deglycosylated forms of FSH. FSH deglycosylation is known to result in inhibitory intracellular events (Arey, et.al., 1997). Thus while the complete structure-function relations of FSH are not yet known, glycosylation is a key structural determinant of function. Hence, use of the present invention to produce large quantities of native glycoprotein hormones is likely to advance detailed studies of structure and function of these hormones. The present invention also provides another source of natural isoforms of native protein hormones for detailed study of their functional roles. Another advantage of the present invention is that cell lines or donors may be tested for viral contamination, including; HIV 1 & 2, HBV, HCV, etc prior to immortalizing the cells, thus providing a safe source of native pituitary hormones.

Additionally, the present invention allows investigation of the molecular biology of pituitary hormone producing cells in vitro without compromise of results due to cellular transformation. For example, determination of the molecular biology of the transforming growth factor family of proteins including activin, follistatin and inhibin is an appropriate application of the immortalized gonadotropes and other target cells. Many of the interactions between regulatory pathways may be altered by transformation. Since the cells of the present invention are not transformed, natural regulatory pathways are intact and suitable for direct investigation. The molecular biology of particular cells may be utilized to optimize expression of a given pituitary hormone and its secretion. Manipulation of these latter parameters effects the specific cellular expression of a given pituitary hormone. Higher levels of specific cellular expression are desirable methods to reduce the cost of the production of a therapeutic product such as cell line-derived FSH. Furthermore, cellular molecular biology may be utilized to extend the functional lifetime in culture, also resulting in a lower production costs.

A final advantage of the present invention concerns the ability to immortalize human pituitary hormone producing cells. While transgenic approaches have been used to immortalize rat pituitary cells at various stages of differentiation, such studies are not realistically applicable to humans because of ethical and regulatory issues regarding transgenic human beings. However, since the present invention utilizes primary cultured cells, including human pituitary cells, such cells may be immortalized and various embodiments of the present invention can be applied to immortalization at different stages of differentiation, given that these can be established in primary culture.

BRIEF DESCRIPTION OF THE DRAWINGS

FIGS. 5A–5C show the growth of different cell lines in athymic mice. (A) shows the results from the positive control, MCF-7 cells. The results obtained from immortalized bovine cell lines, C1+(B) and C3-1 (C) are illustrated. The volume of tumor growth is shown as a function of days post implant. The Y axis scale differs in (A), (B) and (C). Different symbols are from five different mice injected with 10 million cells subcutaneously.

DETAILED DESCRIPTION OF THE INVENTION

Figure 1:
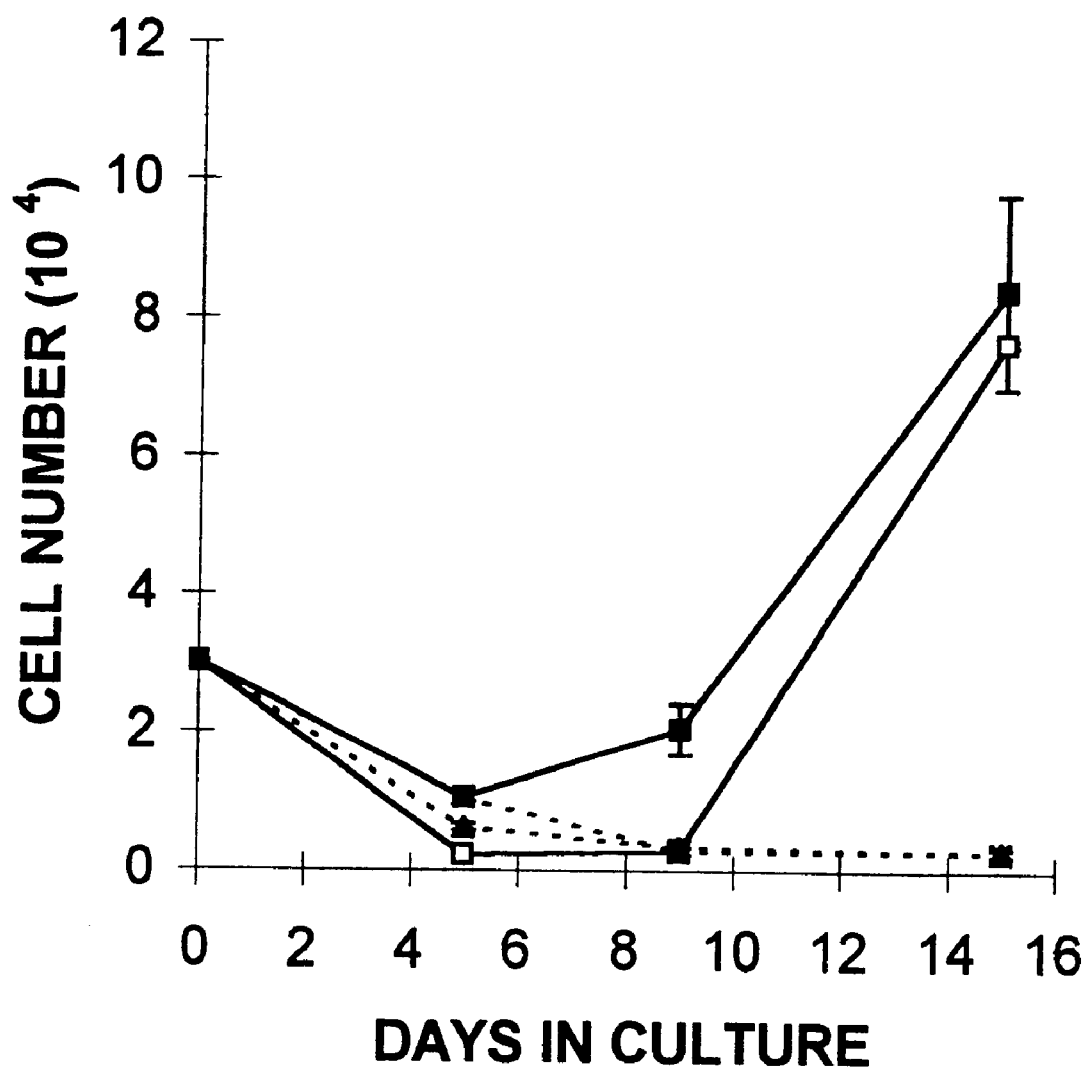
FIG. 1 is a graph of the growth of primary cultures of panned human pituitary cells. The total number of cells determined by hemacytometer is shown as a function of time in different culture media. Cultures indicated by ■ were grown in RPMI-based □ medium. The □ represent cultures grown in medium 199-based Gc medium. The growth of cultures in Opti-MEM alone x or Opti-MEM plus glucose and nonessential amino acids ▼ is also shown.

The methods of the present invention can be performed according to the following steps: 1. Primary culture of dispersed adult or fetal cells. 2. Expansion of the primary cultured cells under defined environmental conditions (also referred to as "environmental factors" herein) including the physical substrate to which attachment-dependent cells attach and the liquid culture medium exposed to said cells. 3. Transfection of primary cultured cells by transfection methods using plasmid DNA containing a DNA vector designed to ensure expression of a foreign gene that induces immortalization including, but not limited to, an establishment oncogene such as viral oncogenes, cellular proto-oncogenes, tumor suppressor gene regulators, or their derivatives. 4. Selection of transfected cells. 5. Characterization of the select genotypic and phenotypic traits of cells which proliferate beyond senescence of wild-type cells maintained in identical conditions. Wild-type cells refer to cells that have not been transfected by plasmids containing foreign DNA establishment oncogenes or their derivatives. The following sets forth the detailed description of the method steps of the present invention.

1. Primary Culture of Dispersed Cells

Primary culture is the means by which cells are established in cell culture according to methods known in the art. For example, a pituitary specimen is collected for primary culture using methods to maximize viability of pituitary cells. Animal pituitary glands may be obtained from a slaughter house at the time of extraction and stored in standard cell culture media, e.g., DMEM/F12. Fetal human pituitary glands are procured according to NIH guidelines for use of human fetal tissue and stored in cell culture media following extraction. The time from extraction to dispersion is less than 24 hours for human pituitary tissue and within 6 hours of extraction for bovine pituitary tissue.

Tissue is dispersed by a combination of mechanical and enzymatic procedures well known in the art. For example, mechanical dispersion occurs first by mincing human fetal tissue with surgical scalpels or by surgical dissection of adult bovine pituitary glands followed by sieving through a small pore screen. Mechanically dispersed human pituitary tissue is then incubated in 1 mg/mL collagenase in culture medium at 37° C. for 45 minutes; dispersed bovine pituitary tissue is treated with 0.2% trypsin, 1 mg/mL hyaluronidase and 1 mg/mL collagenase in physiological saline for 60 minutes at 37° C. Many variations of these dispersion methods are possible and are readily determined by those skilled in the art. Following enzymatic treatment, enzymes are washed from the tissue by use of physiological saline or culture media and separation of the tissue by centrifugation. This wash procedure is repeated as needed to complete enzyme washout.

2. Expansion of Primary Cultured Cells

The dispersed cells are then resuspended in media used for primary culture. Those skilled in the art can readily determine the appropriate media depending on the species from which the cells are derived. For bovine pituitary cells, this media can be, for example, minimum essential media (MEM), 10% Fetal Bovine Serum (FBS), 1% penicillin/streptomycin and 1% mycostatin. For culture of human pituitary cells, useful culture media include, without limitation: a) Serum-free media such as Gc (Hedlund and Miller, 1994) supplemented with commonly used factors well-known in the art. Bovine pituitary cells are plated directly onto standard styrene tissue culture plates.

However, maintenance of hormone secretion from cultured human cells, particularly human pituitary cells, often requires use of extracellular matrix proteins. Purified fetuin is a well-known basement membrane protein that allows maintenance of a well-defined medium. Cruder materials such as matrigel basement membrane matrix is a soluble protein preparation from the Englebreth-Hoth-Swarm mouse sarcoma, a tumor rich in extracellular matrix proteins. Alternatively, human tumor cells elaborating an extracellular matrix, e.g., MCF-7 cells, derived from pleural effusion in 1973 (Soule, et.al., 1973) are initially plated, grown to confluency, ruptured by hypo-osmotic shock and used as an extracellular matrix upon which human pituitary cells are grown.

Growth factor additions to the basal media may include, but are not limited to, activin, tri-iodothyronine, galinin, nerve growth factor, leukemia inhibitory factor, hepatocyte growth factor, acidic or basic fibroblast growth factor, platelet-derived growth factor, pituitary adenylate cyclase-activating polypeptide, vasopressin, retinoic acid, vasoactive intestinal polypeptide. However, it is important to avoid fetal bovine serum, since it suppresses hormone secretion in primary cultured human fetal pituitary cells possibly by inducing terminal differentiation. Growth factor additions are made at any time during the expansion of these cultures to control proliferation and differentiation. The amount or concentration of growth factors, times of exposure, use of multiple growth factors and other conditions can readily by determined by those skilled in the art and depend, for example, on such factors as cell type, species from which the cells are derived, age of the culture and stage of differentiation. The status of differentiation may be determined by a variety of well-known methods in the art such as measurement of the levels of a differentiation-specific protein, e.g, cytokeratin (O'Guin, et.al., 1990).

3. Transfection of Primary Cultured Cells

Figure 3:
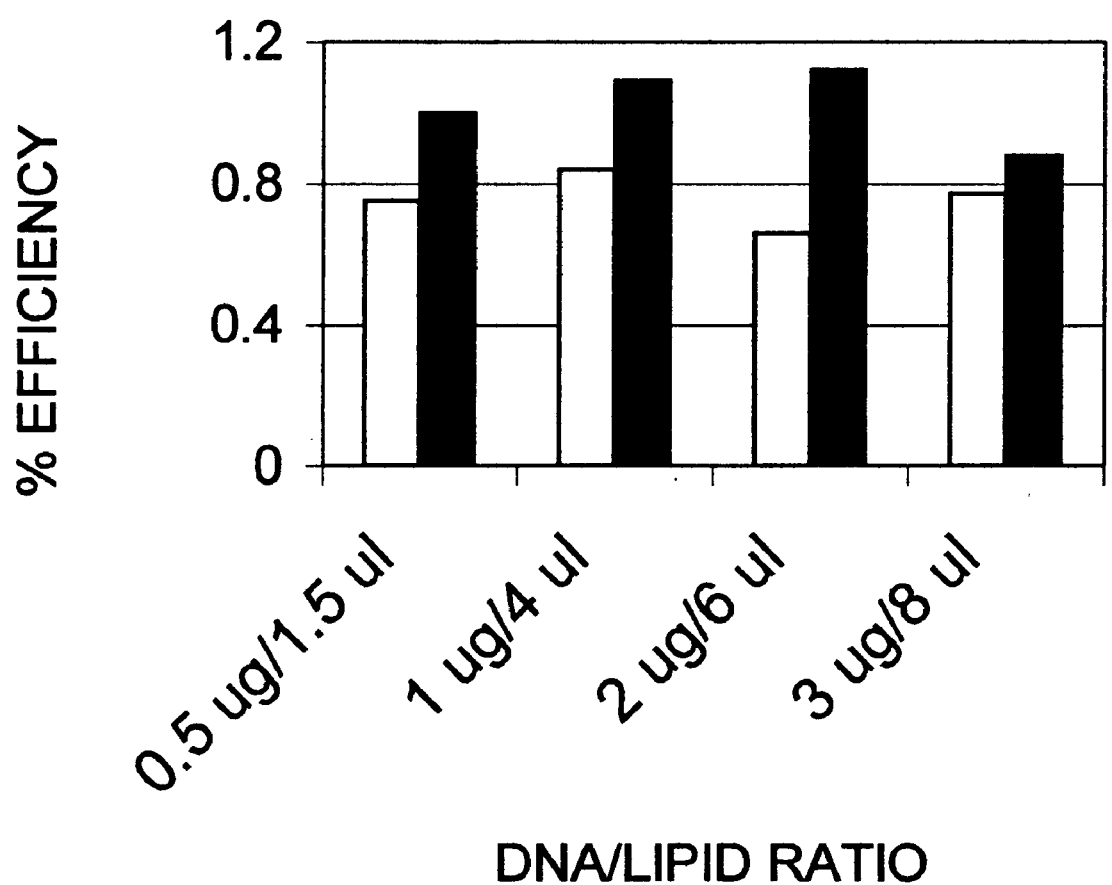
FIG. 3 shows the optimization of liposome-based transfection of bovine pituitary cells using Lipofectin®. Bovine pituitary cells plated 24 hours prior to transfection with reporter plasmid, pcDNA3.1/His/ LacZ (InVitrogen, San Diego, Calif.). The efficiency of transfection is shown at various DNA to lipid ratios in $\mu g/\mu l$ (ug/ul) when the cells were plated at 50,000 cells/ml (open bars) or 30,000 cells/ml (solid bars).

Primary cultured cells are known to be refractory to most transfection systems (Uyttersprot, N, et al., 1998). Therefore, transfection efficiency in cultured pituitary cells was optimized using a plasmid (pcDNA3) containing the β-galactosidase gene and detection of this reporter with X-gal staining method. Liposomes containing cationic lipids (Lipofectin®) were found to be effective in transfecting cultured pituitary cells. FIG. 3 shows the results of optimization of the DNA/lipid ratios at two different plating densities. These data show that 1 to 2 μg DNA per 4 to 6 μl Lipofectin® result in transfection efficiencies slightly greater than 1% when the cells are plated at $3 \times 10^4$ cells/ml. Hence, liposome-based transfection using cationic liposomes such as Lipofectin® is useful for transfecting primary cultured cells. Preferably, transfection efficiency is at least 1%, and more preferably at least 10%. Transfer of genes into primary cells by retroviruses is known to be highly efficient, with transduction efficiencies approaching 100% (Coffin, J M and Varmus, H E, 1996; Ausubel, F M, et.al., 1994). Use of retroviral transfection methods is also useful in the transfection of primary cultured cells according to the present invention.

The concept of targeting liposomal delivery to specific cells by coupling antibodies which recognize unique cell surface antigens is well-known (reviewed by T D Heath and F J Martin, 1986). Efficient coupling of antibody to the liposome requires formation of covalent bonds. Methods employing heterobifunctional cross-linking reagents and covalent linkage to polyethylene-glycol (PEG) moieties of PEG-stabilized liposomes are well-known covalent methods that efficiently form immunoliposomes (Hansen, C B, et.al., 1995; Shwendener, R A, et.al., 1990). The present invention also encompasses plasmid DNA-containing liposomes covalently coupled to antibodies, that are specific to surface antigens of pituitary and other cells, as a method of targeted transfection of primary cultured cells. Such cell surface antigens are, for example, receptor molecules for hypothalamic releasing hormones including, among others, corticotropin releasing hormone (CRH) receptor and the gonadotropin releasing hormone (GnRH) receptor. The distinguishing characteristic of such immunoliposome target antigen is that it is uniquely present upon the surface of a particular target cell and not similarly present on other cells.

The targeted transfection method of transferring plasmid DNA into cultured pituitary cells is applied to mixed cultures of various cells present in the initial cell dispersion and surviving in primary culture. Such mixed cultures are known in the art to maintain intercellular interactions and paracrine effects of endogenous growth promoting factors released from a particular type of cell and acting on other cells. However, another embodiment of the present invention involves use of immobilized antibody to enrich cultures of specific hormone-producing cells. Accordingly, antibodies to specific cell surface proteins including pituitary hormones and receptors for hypothalamic releasing hormones are coupled for example, to magnetic beads, mixed with dispersed cells and separated by magnetic concentration. The antibody-bead conjugate is then detached from cells by incubation in bovine serum albumin (Flaws, J A and Suter, D E, 1993; Valenti, S, et.al., 1995). Separation of cells by cell sorting is also a possibility. The separated cells are then cultured and transfected as described above.

Figure 4A:
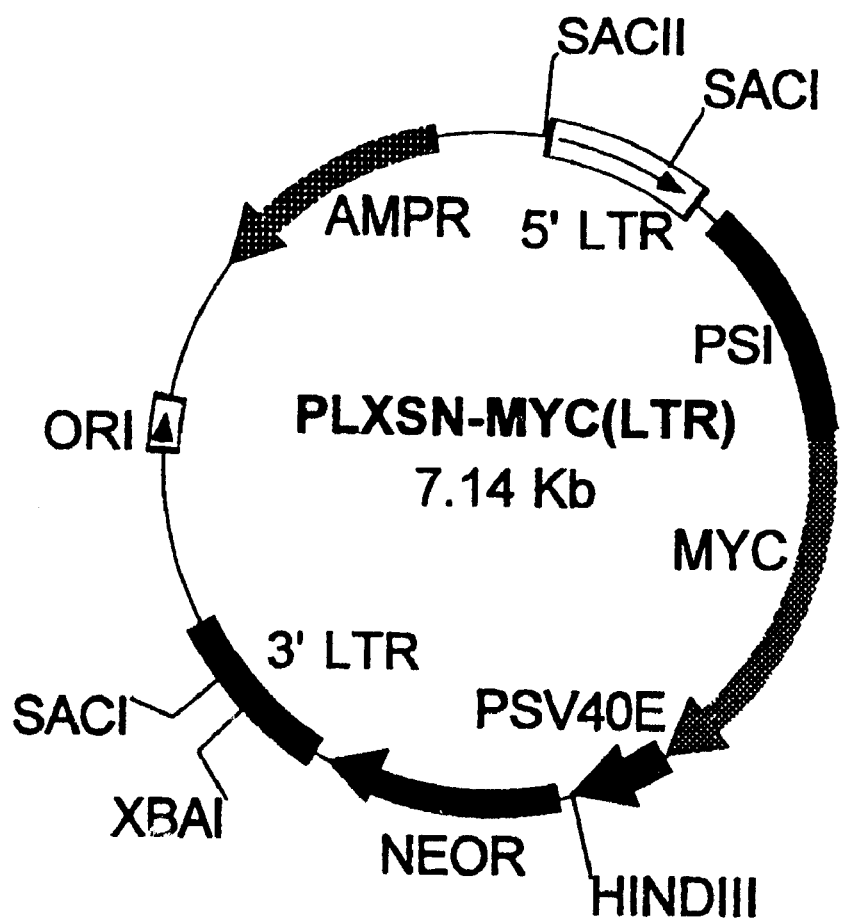
FIGS. 4A–4C depict plasmids in which the myc gene is shown inserted in the pLXSN into the multi-cloning site yielding an expression vector in which the promoter in the 5' LTR drives transcription of the myc oncogene (A). The myc oncogene inserted in the pLXCX2 vector downstream from the constitutive promoter, CMV is shown in (B), while (C) illustrates the myc oncogene inserted into pLXSN where the SV40 promoter element is replaced with an inducible promoter (P) such as a glucocorticoid response element or the tetracycline response element. These plasmids can replicate in bacteria and mammalian cells as well. ψ is the retroviral recognition site for packaging of these plasmids in a helper strain of cells which provides the viral coat proteins.
Figure 4B:
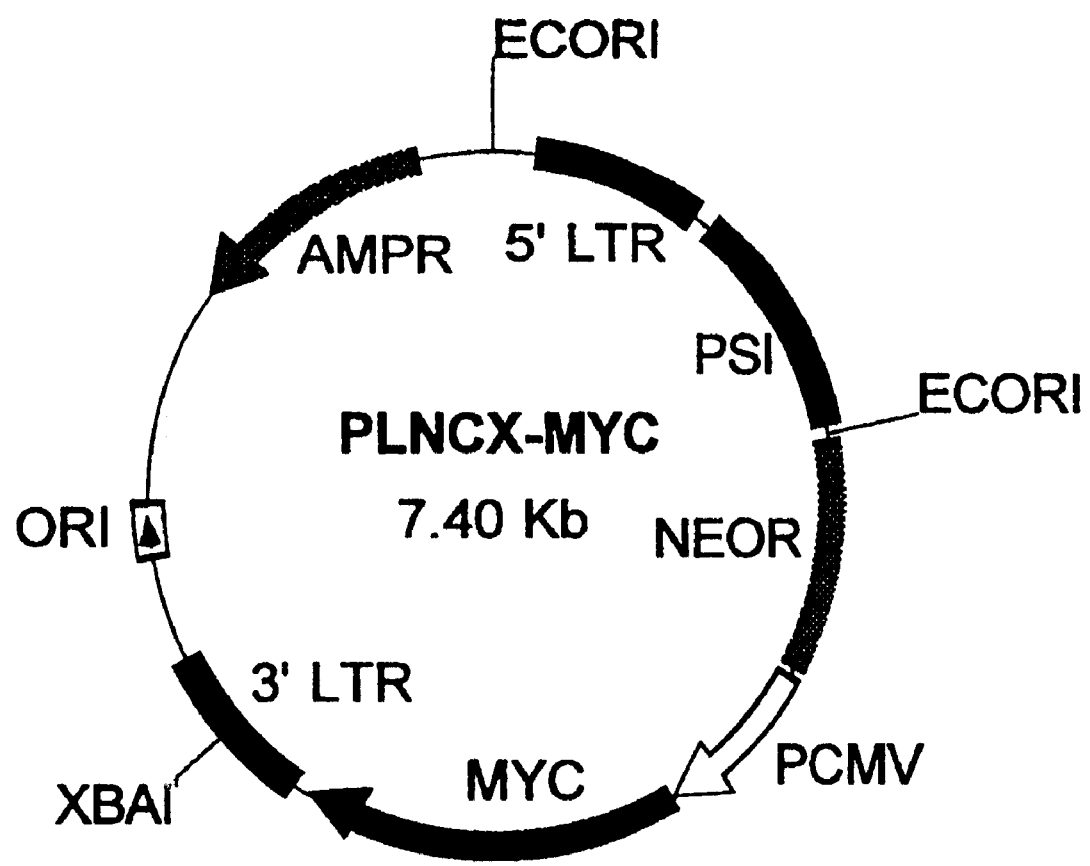

The present invention includes the use of suitable plasmid DNA that is transferred into target cells by transfection methods outlined above to achieve immortalization of cultured pituitary cells. Plasmid DNA is composed of a vector and a foreign gene or genes. The vector is designed to support the expression of foreign DNA and its integration into to the genome of transfectants. The vector used to support expression of the foreign DNA is composed of various DNA sequences well-known in the current art of molecular biology. For example, a suitable expression vector is pcDNA3 (In Vitrogen, Inc., San Diego, Calif.) which contains the enhancer-promoter sequences of the immediate early gene of human cytomegalovirus (CMV) upstream from various subcloning sites, a neomycin resistance gene and prokaryotic sequences permitting growth and selection in microorganisms. Other eukaroytic vectors capable of stable transfection, preferably containing the SV40, CMV, thymidine kinase (TK) or Rous sarcoma virus (RSV) promoter immediately upstream from the subdloning site, are within the scope of the present invention. These vectors include, without limitation, known retroviral expression vectors such as pLNCX2 and pLXSN (See FIG. 4). Also, the use of endogenous promoter sequences specific to normal pituitary cell expression such as the α subunit promoter engineered to drive the expression of the SV40 Large T antigen (Mellon, P1, et.al., 1991), may also be used to transfect primary cultured pituitary cells. The foreign gene to be expressed in transfectants is subcloned into suitable subcloning sites of the expression vector using well-known methods. As an aid in subcloning into the expression vector, primers used for polymerase chain reaction (PCR) of specific target genes are synthesized to include restriction endonucleases near the 5' ends according to the subcloning sites available on the expression vector.

Expression vectors containing a variety of subcloned foreign genes are encompassed in the present invention; the result of expression of these genes within transfectants is controlled proliferation of transfected cells without ensuing malignant transformation. These genes include, but are not limited to, known establishment oncogenes: (a) viral oncogenes, including, for example, the large T antigen of SV40, the Epstein-Barr virus and the E7 gene of the human papilloma virus, (b)cellular proto-oncogenes including, for example, gsp, gip2 (Barlier, A.,et al., 1997), myc andfos, pituitary tumor-transforming gene (Zhang, X, et.al., 1999) and c) tumor suppressor genes, including, for example, MEN1, MEN2a and MEN2b (Chakrabarti, R, et al., 1998), p53 and p105-Rb. Derivatives, including those resulting from mutation or deletion of specific sequences of the above listed genes are also encompassed herein. For example, pituitary cells derived from animal species can be transfected with the SV40 large T antigen, while human pituitary cells are more preferably transfected with expression vectors encoding sequences of c-myc, v-myc, N-myc, L-myc or derivatives thereof. Inherent in this embodiment of the present invention is regulated over expression of myc allowing for controlled cell division without apoptosis, as opposed to unregulated myc over expression as occurs in oncogenic transformation.

Figure 4C:
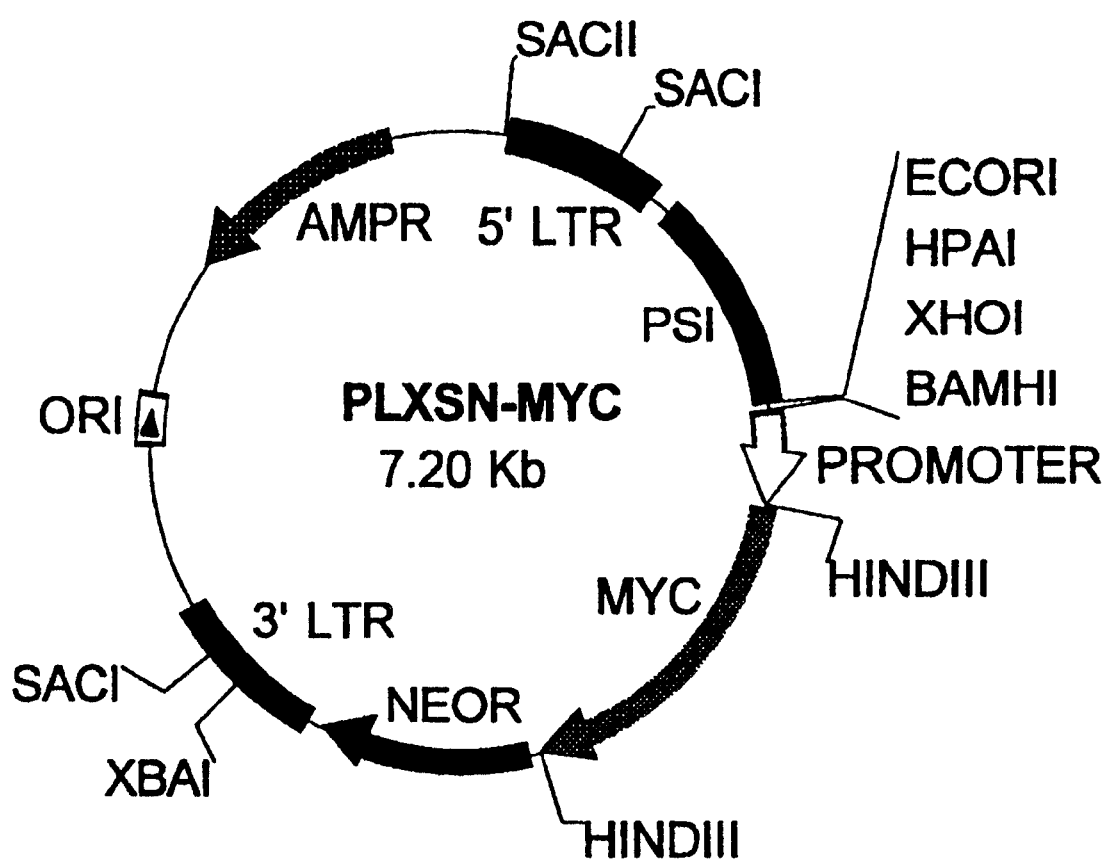

One of four methods described below can be used for regulated expression of foreign myc transcripts within transfectants. The first method involves the use of specific promoters resulting in regulated expression, including for example, SV40, CMV, TK or RSV. The second method involves inducible myc expression by use of expression vector promoters, e.g., β-galactosidase, T7, chloramphenicol, mouse metallothionein (MT) promoter (Kelly, et.al., 1997), the glucocorticoid promoter, and tetracycline response elements. The construction of an inducible promoter is shown in FIG. 4C. Inducible promoters are activated by small, non-toxic molecules such as, but not limited to, isopropyl-β-D-thioglactopyranoside (IPTG), added to culture media (Wang, Q, et.al., 1992; Films, et.al., 1992) or $Zn^{2+}$. The presence of an inducer drives the expression of myc inducing immortalization of pituitary cells. When the inducer is removed from cultures the immortalized cells revert to their differentiated state having all the control mechanisms and machinery for production of hormones. An example of this negative control of differentiation is seen in immortalized human dorsal root ganglia cells where the cells return to their neuronal phenotype when the inducing molecule for oncogene expression is removed from the culture (Raymon, H K, et.al., 1999). The third method involves the controlled expression of endogenous c-myc, as for example, by use of components of the Wnt pathway, including Wnt receptor agonists. Finally, the fourth method involves the genetic alteration of the foreign myc cDNA to alter its biological activity, including but not limited to, site-specific mutagenesis resulting in $Ser^{62}$ substitution which selectively inhibits the transforming activity of myc (Pulverer, B J, et.al., 1994).

Another embodiment of the present invention is the promotion of cell proliferation by environmental factors such as exposure to proliferation-inducing growth factors, for example, activin which is a specific growth factor for gonadotropes (Katayama, T, et.al., 1990),tri-iodothyronine, galinin, nerve growth factor, leukemia inhibitory factor, hepatocyte growth factor, acidic or basic fibroblast growth factor, platelet-derived growth factor, pituitary adenylate cyclase-activating polypeptide, vasopressin, retinoic acid, vasoactive intestinal polypeptide. Environmental factors also include genetic manipulations outlined above, together with genetic blockage of apoptosis. For example, over expression of the Bcl2 gene is known to block apoptosis (Adams, J M and Cory, S, 1998). Hence, transfection with plasmids containing the cDNA for Bcl2 resulting in its over expression is an alternative means of immortalization of proliferating pituitary cells.

Subsequent to immortalization of pituitary hormone-producing cells, genetic alterations resulting in enhanced hormone expression, altered hormone glycosylation, and variation of the hormone amino acid sequence may be desirable depending upon the particular application of the present invention. Hence, the present invention also includes genetic alterations of a specific immortalized pituitary cell line, including, but not limited to: those alterations resulting in enhanced expression of endogenous hormone(s), altered amino acid sequence of the expressed hormone, and altered glycosylation of the pituitary glycoprotein hormones.

5. Selection and Expansion of stable Transfectants

Selection of transfectants can be accomplished by the survival of immortalized cells beyond senescence, or by the transfection of an antibiotic resistance gene within the plasmid used to induce immortalization. For example, inclusion of the neomycin-resistance gene within the expression vector allows for selection of transfectants by growth in media containing toxic levels of geneticin (G418). Furthermore, continued expansion of transfectants in selective media is a well-known method in the art for selective expansion of plasmid-containing cells and maintaining stable transfection. Using targeted transfection to specific types of hormone-producing cells, for example, further enhances selectivity in that clonal cultures of hormone-producing cells may be established. In applications of the present invention on mixed cultures without targeted transfection methods, clonal selection of pure hormone-producing cell types, e.g., somatotropes, may be accomplished by cloning methods well-known in the art such as use of a cloning ring or limiting dilution. Furthermore, use of defined cell culture media (i.e., the use of environmental factors as described above) is preferable during expansion of transfectants to maintain controlled states of proliferation and differentiation.

6. Characterization of Transfected Cells

Methods well-known in the art of cell culture are used to monitor and characterize transfected pituitary cells. Cellular viability is measured by standard methods of doubling time determination. Passage number is also determined. Survival beyond senescence of wild-type cells is a standard indicator of immortalization. However, secondary senescence or appearance of crisis stage following survival beyond senescence is common in cells transfected with establishment oncogenes. Immortality generally refers to cell lines which have substantially outlived senescence, both primary and secondary. As used herein, immortality refers to continued maintenance of cell viability at a 5-fold greater passage number than senescence with maintenance of steady doubling times throughout this growth period. For example, expression of the protein/peptide pituitary hormones is an important phenotypic trait that the present invention is designed to maintain. Hormone expression is commonly measured by assaying hormone secretion into culture media. This requires the use of quantitative, highly sensitive assays that have been rigorously validated. Such assays are not readily available commercially for animal hormones but several such assay systems are available for human pituitary hormones because of the clinical significance of these measurements. Alternatively, expression of hormones in immortalized cells can be determined by measurements of messenger RNA encoding specific hormones as by reverse transcriptase PCR (RT-PCR) or Northern blot analysis. Similarly, well-known methods are used to measure receptors for hypothalamic releasing hormones and expression of differentiation factors of known importance in the differentiation of pituitary hormone-producing cells such as Pit1 and SF-1 (Simmons, D M, et.al., 1990; Sanno, N, et.al., 1998; Bedford, et.al., 1996). Such measurements are important indicators of the status of differentiation of cultured pituitary hormone-containing cells. Analysis of additional markers of differentiation including cytokeratins also provides information on the developmental status of the immortalized cells (O'Guin, et.al., 1990). Transformation is assessed by standard methods well-known in the art including in vitro assays such as growth of cells in semi-soft agar and in vivo assays using growth in nude mice as indicative of the transformed phenotype. Additional methods to determine the presence and expression levels of foreign DNA are also well-known, such as RT-PCR and Northern blots. Determination of the molecular size of genetic material containing probed sequences with and without exposure to specific endonucleases may be used to determine whether foreign DNA has been integrated into the host cell genome.

The following examples illustrate, but not limit, the present invention.

EXAMPLE 1

Primary Culture of Pituitary Cells

A. Primary Culture of Bovine Pituitary Cells

Fresh bovine pituitary glands were received from G&C Packing Co. (Colorado Springs, Colo.) within 6 hours of extraction. These were handled aseptically with sterile solutions throughout as follows: 1) Extraneous tissue was removed and the glands were quickly immersed in 70% ethanol and rinsed with Krebs-Ringer buffer solution containing 0.5% BSA, 100 U/ml penicillin and 100 $\mu$g/ml streptomycin (Sigma Chemical Co., St. Louis, Mo.). 2) The glands were mechanically dissociated by mincing with a scalpel and sieving through a metal screen. 3) The homogenate was then treated with Krebs-Ringer buffer containing 0.2% trypsin, 1 mg/ml hyaluronidase and 1 mg/ml collagenase (Sigma Chemical Co., St. Louis, Mo.) for 60 minutes at 37° C. with agitation. 4) Enzymes were washed from dispersed cells by suspension in Krebs-Ringer buffer and centrifugation (10 minutes at 48×g) of pituitary cells. 5) Pelleted cells were resuspended in minimum essential medium (MEM) containing 5% FBS, 100 U/ml penicillin, 100 $\mu$g/ml streptomycin and 1% mycostatin. 6) Cells were plated in 6 well culture plates (Nalge Nunc International, Rochester, N.Y.) using 1 pituitary gland per 4 wells; about $1\times10^5$ cells per ml and maintained in humidified air, supplemented with 5% $CO_2$ at 37° C. Plated cells were visualized with an inverted, phase contrast microscope.

B. Primary Culture of Human Pituitary Cells

Fetal human pituitary glands were obtained from Anatomical Gift Foundation (White Oak, Ga.) or Advanced Bioscience Resources, (Alameda, Calif.). Pituitary glands were stored in approximately 20 mls of RPMI culture media at 4° C. and processed within 24 hours of dissection. The gestational age ranged from 19 to 24 weeks. The following dispersion procedure was performed using sterile materials and technique throughout. Tissue was rinsed in 30 mls modified Kreb's Ringer solution, supplemented with 5 g/L bovine serum albumin (BSA) and nonessential amino acids. The tissue was then transferred to a glass microscope slide, and finely minced using scapels. Minced tissue was suspended in 2 to 2.25 mls modified Kreb's Ringer containing 1 mg/ml collagenase (Sigma Chemical Co., St. Louis, Mo.). The mixture was incubated at 37° C. with rotation at 250 rpm for 60 minutes. The dispersed cells were washed in 20 mls DMEM/F12 medium and centrifuged (5 minutes at 428×g). The supernatant was aspirated leaving 2–4 mls, and two additional washes were performed using 10 mls DMEM/F12. Cells were counted using a hemacytometer (Fresney, I R, 1987). The total number of cells ranged from 100,000 to 2 million per gland, with greater cell numbers in older pituitary glands. The mixture was centrifuged (5 minutes at 428×g). The pellet was then resuspended in culture media, as described below, at approximately $10^5$ cells/ml and plated into multi-well, styrene tissue culture plates, incubated at 37° C. in humidified air supplemented with 5% $CO_2$.

Primary culture conditions necessary for the proliferation of endocrine cells of the pituitary gland were investigated. The present invention requires cellular proliferation of target cells for integration of foreign DNA into the host cell genome and induction of immortalization. The pituitary gland is composed of numerous cell types including fibroblasts, follicular stellate cells, endocrine epithelial cells (gonadotropes, thyrotropes, somatotropes, lactotropes, melanotropes, corticotropes) and endothelial cells from blood vessels. Since the hormone-producing endocrine cells are one target of the present invention, we investigated methods to enrich the population of endocrine cells. Fibroblast cells may be significantly depleted from primary cell cultures by differential adsorption to tissue culture plates, a method known as "panning". Primary cultures were panned by initially plating the dispersed pituicytes in a single 35 mm tissue culture dish at about $5 \times 10^4$ cells/ml. After 16–24 hours, less adherent cells were removed from these cultures by repetitive pipetting of media (approximately 10 times). These cells were pelleted by centrifugation (5 minutes at 428×g) and replated at $10^5$ cells/ml. Centrifugation at lower g forces resulted in incomplete recovery of cells from the pellets. Hormone assay results and immunohistochemical staining showed that the hormone-producing cells were enriched in the less adherent cell population while fibroblast cells were more strongly adsorbed. While this panning method did not result in complete separation of fibroblast and endocrine cells, somatotropes and gonadotropes were significantly enriched within the panned cultures.

Experiments were first performed to investigate the effect of different culture media on the growth of endocrine cell-enriched cultures. We investigated a commercially available medium, Opti-MEM (Life Technologies, Rockville, Md. with and without additional glucose (50 mg/ml and non-essential amino acids (Sigma Chemical Co., St. Louis, Mo.). We also tested a serum-free defined media, Gc, that has been used in the primary culture of human prostate epithelial cells (Hedlund and Miller, 1994). The modified Gc media tested here utilized either RPMI 1640 or Medium 199 (Life Technologies, Rockville, Md., 20 µg/ml bovine insulin, 10 µg/ml human apo-transferrin, 25 nM sodium selenite, 0.5 mM sodium pyruvate, 2 mg/ml BSA (Cohn fraction V), 10 mM HEPES, 0.5 mg/ml fetal bovine fetuin, 50 nM hydrocortisone, $10^{-10}$ M Tri-iodothyronine (T3), 1 ng/ml human recombinant EGF (Intergen, Co., Purchase, N.Y.). Unless otherwise indicated, all reagents were purchased from Sigma Chemical Co. (St. Louis, Mo.). Cell growth was determined by periodic cell counts using a hemacytomer of less adherent cells that were removed by multiple pipetting. The results are shown in FIG. 1. There was an initial decrease in the total number of cells at five days with all media tested. Opti-MEM failed to support growth regardless of additional glucose or amino acids (broken lines). RPMI-based Gc media supported maximal logarithmic growth apparent between days 5 and 15. The Gc media and additions resulted in approximately 5-fold increases in the total cell population at 15 days (solid lines). The RPMI 1640-based Gc medium was chosen for additional study because of its ability to support growth.

To monitor the viability and/or secretory capability of the hormone-producing endocrine cells, we measured secretion of pituitary hormones from cultures of panned pituitary cells. The level of FSH, LH, prolactin and TSH in culture media was determined using an automated chemiluminescent-based immunoanalyzer, ACS: 180™ (Chiron Diagnostics, Inc., Norwood, Mass.). Growth hormone was determined using an immunoradiometric assay (Nichols Institute, San Juan Capistrano, Calif.). Culture media was harvested on Mondays and Fridays from growing cultures for several weeks. These cultures were maintained in 48-well plates (Falcon/Becton Dickinson, Franklin Lakes, N.J.), with each well containing 1 ml of media. The majority of the media were carefully removed to avoid uptake of cells and transferred to 12×75 mm tubes for analysis. Cells were fed with an equal volume of fresh medium at the same time points. Background levels of GH in various media were insignificant (<0.1 ng/ml). Each condition was tested in duplicate and graphed values are the mean hormone concentration +/– standard deviation.

Figure 2:
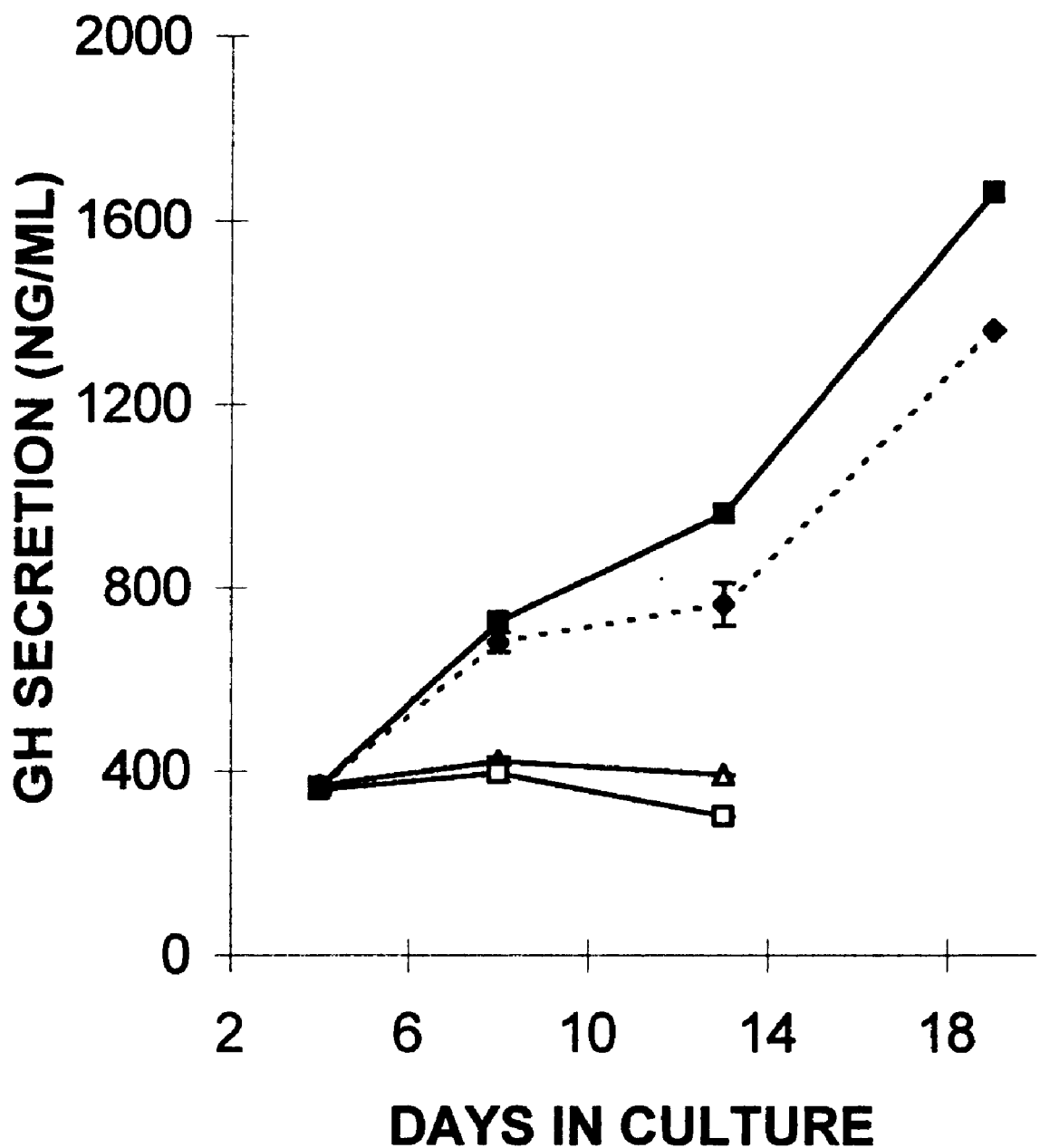
FIG. 2 shows the effects of different media on growth hormone secretion from panned human pituitary cells. Growth hormone secretion in ng/ml is shown as a function of days in culture for first passage cells. The effects of RPMI-based Gc medium with estradiol on monolayer cultures ■ or spheroid cultures ♦ is compared to DMEM/F12-based Gc media with Δ or without ▲ estradiol.

FIG. 2 shows the secretion of GH by panned pituicyes over the course of 15 days in various media. Estradiol ($10^{-10}$ M) was included in the media since previous experiments indicated its stimulatory effect on GH secretion. Monolayer cultures of pituicytes showed continual increases in GH secretion over 19 days, while confluence was reached at 12 days. We also tested a three-dimensional spheriod culture technique (Hedlund, T E, et.al., 1999) using the same Gc medium with estradiol. While spheriod cultures have been used to promote differentiation of many primary cultures, there was no apparent effect on GH secretion. RPMI-based Gc media resulted in higher levels of GH secretion than DMEM/F12 based-media with or without estradiol (See FIG. 2).

Similar types of experiments were done to optimize cell culture conditions and components for secretion of GH, FSH, LH, and prolactin from primary cultured human pituitary cells. The results are shown in Table 1. The tissue culture conditions investigated included the base media for Gc, addition of non-essential amino acids (NEAA) to the media, panning in Gc media and spheriod 3D culture, as described above. We also investigated pituicyte growth on plastic coated with Matrigel (Collaborative Biomedical Products, Bedford, Mass.). However, the inability to manipulate these cultures for propagation, transfection and immunostaining precluded its use. Also investigated were three hormones from the steroid receptor superfamily including: hydrocortisone, 17β-estradiol, and T3. While $10^{-10}$ M T3 was beneficial to the secretion of GH, LH and prolactin, it was strongly inhibitory to TSH release probably because of its well-known inhibitory effect on TSH gene transcription in thyrotropes.

TABLE 1

Optimum Conditions for Pituitary Hormone Secretion from Primary Cultures

|  | GH | FSH | LH | PRL |
|---|---|---|---|---|
| GENERAL T.C. CONDITIONS | | | | |
| Base medium for Gc | RPMI | RPMI | DMEM/F12 | RPMI |
| Nonessential amino acids | + | + | + | NE |
| Panning | + + | + + | + | NE |
| Spheriod 3D Culture | No advantage | – | – | No advantage |
| STERIOD HORMONE SUPERFAMILY | | | | |
| Hydrocortisone | $5 \times 10^{-8}$M | $5 \times 10^{-8}$M | NE | NE |
| 17β-Estradiol | $1 \times 10^{-10}$M | NE | NE | $1 \times 10^{-10}$M |
| Y3(3,5,3' triiodothyronine) | $1 \times 10^{-10}$M | NE | $1 \times 10^{-10}$M | $1 \times 10^{-10}$M |
| PEPTIDE HORMONES & GROWTH FACTORS | | | | |
| GnRH | NE | $10^{-10}$M | $10^{-7}$ to $10^{-10}$M Similiar effect | NE |
| FGF-basic | 0.1 ng/ml | NE | NE | NE |

Abbreviations used in Table 1: T.C., tissue culture; NE, no effect detected; +, stimulatory; –, inhibitory.

We also investigated the effects of hypothalmic releasing hormones and select growth factors on pituitary hormone secretion. While there are reports of beneficial effects of platelet-derived growth factor (AA & BB) and FGF-acidic & basic (Leon, SP, et.al., 1994; Ericson, J, et.al., 1998) on cultured pituitary cells, we have preliminary evidence to suggest that 0.1 ng/ml FGF-basic potentiates GH release. All other conditions were found to produce no detectable effect on GH, FSH, LH and prolactin release. GnRH (gonadotropin releasing hormone) was also tested in the presence of cortisone and estrogen. Both FSH and LH secretion were significantly potentiated with the initial treatment, while repeated application of GnRH was progressively less effective. A concentration of $10^{-10}$ M GnRH was best for FSH and LH was effected by all concentrations tested. For this reason there appears to be no long-term advantage for including GnRH in the medium formulation. Hence the data shown in Table I enabled us to create an optimal medium for maintaining the secretion of GH, FSH, prolactin by pituicytes in culture. LH secretion, however, was poorly maintained even with conditions found to be optimal for FSH. This may reflect instability of the secreted LH and/or the lack of necessary factors to maintain LH secretion.

EXAMPLE 2

Expansion of Primary Cultured Pituitary Cells

A. Expansion of Bovine Pituitary Cultures.

Confluent cultures were incubated with 0.025 mg/ml trypsin with EDTA (Life Technologies, Inc., Rockville, Md.), centrifuged (10 minutes at 47×g) and subcultured at $1\times10^{-5}$ cells/ml in small T-flasks (T-25). After 3 to 5 passages, these cultures exhibited signs of senescence including the appearance of large vacuolated, multi-nucleated cells and a reduced growth rate.

B. Expansion of Human Pituitary Cultures.

Confluent cultures were exposured to low levels of trypsin (0.0025 mg/ml trypsin in 0.05 mM EDTA; Sigma Chemical Co., St. Louis, Mo.) for 30 seconds to 1 minute. This reaction was immediately stopped by the adding an equal volume of 0.2 mg/ml soybean trypsin inhibitor (Sigma Chemical Co, St. Louis, Mo.). Cell viability was diminished by failure to inhibit trypsin. Cells were washed once by centrifugation (5 minutes at 428×g) and were subcultured at $10^5$ cells/ml. These cultures continued to grow at similar rates through 3 passages. By the fifth passage, little further growth was observed even with prolonged culture. Hormone secretion was found to decrease with sequential passaging. Growth hormone secretion diminished by 50%, 85% and 100% in passages 2, 3 and 4 respectively. Secretion of FSH and prolactin diminished similarly. Hence, using these methods, senescence of primary cultured human pituitary cells occurs near the $5^{th}$ passage.

Flow cytometric immunofluorescence was used to determine the percentage of first passage cells expressing growth hormone after 19 days in primary culture. Cells were prepared by incubating in a chelating buffer (135 mM NaCl, 5 mM KCl, 20 mM Hepes, 1.5 mM EDTA, pH 7.4) and repeatedly pipetted to detach the cells from culture plates. Large aggregates of cells were allowed to settle out for 1 minute. The suspended cells were fixed in an equal volume of Zamboni fixative (Hatfield, J M and Hymer, W C, 1985) for 20 minutes at room temperature and then washed three times in 10 mls PBS by centrifugation (5 minutes at 428×g).

The final pellet was resuspended in 1 ml PBS, 5% goat serum and 0.1% sodium azide. Incubation in serum continued for 10 minutes at room temperature to block nonspecific binding. After centrifugation, the cells were incubated with either of two primary antibodies at 2 pg/ml: a mouse monoclonal antibody to GH (Biogenesis, Inc., Catalog No. 4750–0280) or a nonspecific mouse $IgG_1$ (Dako Corp., Catalog No. X-0931). These mixtures were agitated every 10 minutes for the first half hour and then incubated overnight at 4° C. The cells were then washed three times with PBS containing 1% BSA and 0.1% azide.

The cells were reacted with the secondary antibody, FITC-conjugated goat anti-mouse Ig (Dako Corp., Catalog No. F-0479) at 50 μg/ml. The cells were incubated at room temperature for 30 minutes and washed twice with PBS. The final pellet was resuspended in 500 μl PBS, 1% BSA, 0.1% sodium azide and stored at 4° C. in the dark until flow cytometric analysis.

The cells were analyzed on a Mo Flow (Cytomation, Inc., Fort Collins, Colo.) flow cytometer. Forward and side-scatter profiles were used to gate intact, single cells. The fluorescence of nonspecific and growth hormone-stained cells was quantitated and compared. The percent positive cells were monitored, setting the nonspecific at 2.9% and subtracting it from the final number. This analysis indicated that 34% of the pituicytes were positive for growth hormone. Furthermore, the mean fluorescence of the GH-stained cells was 11-fold brighter than the nonspecifically stained population. These results indicate that at least one third of our expanded pituitary cultures express growth hormone after 19 days in culture. This percentage of somatotropes is very similar to that of the intact, adult pituitary gland.

The percentage of proliferating cells in the human pituitary cultures was also quantitated using flow cytometry. We utilized live cells from the suspension described above for GH staining. Approximately $5 \times 10^4$ cells were pelleted and resuspended in 500 $\mu$l of propidium-iodide solution containing saponin and RNAse (Hedlund, et.al., 1998). The proliferating cell population was quantitated by adding together the S-phase and $G_2$/M peaks. Approximately 17% of the cells were proliferating at this time point. This relatively high mitotic rate was critical to maximize transfection efficiency for subsequent immortalization of primary cultured human pituitary cells.

EXAMPLE 3

Transfection of Cultured Pituitary Cells
A. Transfection of Bovine Pituitary Cells.

Transfection efficiency in cultured pituitary cells was determined using the pcDNA3 plasmid containing the β-galactosidase gene (In Vitrogen, Inc., San Diego, Calif.) and colorimetric detection of galactosidase activity in cultured cells. Liposomes containing cationic lipids (e.g., Lipofectin®; Life Technologies, Inc., Rockville, Md. were found to be effective. FIG. 3 shows the results of optimization of the DNA/lipid ratios at two different plating densities. These data show that 1 to 2 $\mu$g DNA per 4 to 6 $\mu$l Lipofectin® result in transfection efficiencies slightly greater than 1% when the cells are plated at $3 \times 10^4$ cells/ml. Liposome-based transfection using cationic liposomes such as Lipofectin® results in successful transfection of primary cultured bovine pituitary cells. The third pass culture of primary bovine pituitary cells were transfected at 60 to 70% confluency in the wells of a 24 well plate. The transfection volumes of each well were 0.4 ml of DMEM/F12 medium, which contained 0.5 $\mu$g of pSV3neo plasmid and 1.5 $\mu$l of Lipofectin®. The transfection solution was replaced 16 hours later with complete growth medium which is replaced every 2 to 3 days.
B. Transfection of Human Pituitary Cells.

Dispersed and panned cells human pituitary cells were plated at 200,000 to 300,000 cells per ml in 6-well plates (Falcon/Becton Dickinson, Franklin Lakes, N.J.) and grown until 30–50% confluent. Transfection was performed using cationic lipids to deliver plasmids containing either the SV40 large T antigen or the v-myc oncogene into primary-cultured pituitary cells. Plasmids without oncogenes were used as controls for transfection. Wells transfected with control plasmid slightly outlived primary cell cultures due to the presence of the gene coding for G418 resistance but died after 2 to 3 weeks or a single passage of the cells. Using Lipfectin®, we transfected panned pituitary cells with either pSV3neo (Southern, P J and Berg, P J, 1982) or pLXSN-v-myc, constructed as described below. The concentration of DNA was kept constant (typically 1–2 pg) in each well while the amount of cationic lipid increased from 0–20 $\mu$l. The plasmid (1–2 $\mu$l) was mixed with 100 $\mu$l of Gc medium and incubated for 45 minutes at room temperature. Increasing amounts of Lipofectin® (2–20 $\mu$l) were also mixed with 100 $\mu$l of medium and incubated for 45 minutes at room temperature. The two solutions were then combined, mixed gently and incubated for 30 minutes at room temperature. The panned cells were then washed with Gc medium and 0.8 ml of fresh medium was added to each well. For each transfection, we then added 0.2 ml of the Lipofectin®/DNA mixture using gentle swirling of the plates to distribute the complexes. The transfection mixtures were allowed to incubate at 37° C. for 8 to 12 hours before replacing the medium with 2 ml of fresh Gc medium. After 48 hrs, Gc medium was replaced with Gc medium containing 0.5% FBS and 150 $\mu$g/ml G418. The formation of colonies in the presence of G418 was monitored for a varying number of weeks. We found that 150 $\mu$g/ml G418 was sufficient to kill all primary pituitary cultures tested.

EXAMPLE 4

Plasmids used to Immortalize cultured Pituitary Cells
A. pSV3neo Plasmid.

The pSV3neo plasmid was obtained from the American Type Culture Collection (ATCC), Rockville, Md.

This plasmid was prepared from *E. coli* (HB101) cell lysates. Plasmid DNA was purified using standard miniprep techniques well-known in the art.
B. Cloning the v-myc Gene into the Retroviral Vectors, pLXSN and pLNCX2.

The plasmid, pSVv-myc, containing a fusion of the gag and v-myc genes (Land, et.al., 1983; provided by Dr. Robert Weinberg, Whitehead Institute of Biomedical Research, Cambridge, Mass.) was amplified by PCR to obtain the v-myc gene sequence for cloning into two retroviral vectors, pLXSN which contains a weak promoter in the 5' LTR region and pLNCX2 (See FIG. 4) which contains a constitutive promoter, CMV (Clonetech, Inc., Palo Alto, Calif.). Having both a weak promoter and a strong promoter to drive production of v-myc allows for two different levels of oncogenic protein that may have different effects in the immortalization of pituitary cells.

The cloning steps are shown below for both pLXSN and pLNCX2 derivatives. The same primer set was used for both PCR amplification of v-myc and cloning into pLXSN. The 5' primer contains an EcoRI site (underlined) and a start codon (residues 16–18) as follows: 5'-CGAGCGGAATTCGCCATGGTGCACGGCCAGGC AGC-3' (SEQ.ID.NO.1). The 3' primer contains a BamHI site (underlined) and a stop codon (residues 13–15): 5' CGAGCGGGATCCCTATGCACGAGAGTTCCTTAGC TGCTC-3' (SEQ.ID.NO.2). These oligonucleotides at 1 $\mu$M were used for PCR in the presence of 4 units of Taq DNA polymerase (Promega, Cat. No. M1665), 10 mM Tris-HCl (pH 9), 50 mM KCl, 0.1% Trition X-100, 1.5 mM $MgCl_2$, 200 $\mu$M dNTPs and 101% DMSO to obtain the v-myc gene sequence for cloning. Thirty cycles of PCR were performed as follows: 1 minute at 94° C. for denaturation, 1 minute at 66° C. for annealing, and 3 minutes at 72° C. for extension. The resulting product and the pLXSN vector were then cut with an excess of EcoRI and BamHI overnight at 37° C. The DNA digests were purified using a PCR purification kit (Qiagen, Inc., Cat No. 28106). The cut vector and PCR product (about 1300 bp) were mixed at a 1:3 molar ratio and ligated overnight with T4 DNA Ligase (Promega, Inc., Cat No. M1804) at 16° C. The ligation mixtures were then diluted 1 to 10 and for transformation of competent DH5α cells (Life Technologies, Inc., Cat. No. 18265–017). Transformants were selected on LB agar containing 100 $\mu$g/ml ampicillin. Individual clones were expanded and plasmid DNA was isolated using well-known miniprep techniques. Diagnostic restriction digests were performed using EcoRI, BamHII and SalI. Cleavage with SalI in combination with the original enzymes used for cloning, EcoRI and BamHII, yielded 600 and 700 bp fragments that were diagnostic for the presence of v-myc since the SalI site is not present in the pLXSN vector. One clone was selected and sequenced. It showed complete homology to the reported gene sequence of v-myc (Atitalo, K, et. al., 1983). The resultant vector, pLXSN-v-myc was used to transfect primary cultured pituitary cells using the methods described in the previous section.

Primers for PCR and cloning of the v-myc gene into the pLNCX2 vector differ only in the restriction sites used for cloning. The 5' primer contains a HindIII site (underlined) and a start codon (residues 16–18) as follows: 5'-CGAGCGAAGCTTGCCATGGTGCACGGCAGGCA GC-3' (SEQ.ID.NO.3). The 3' primer contains a StuI site (underlined) and a stop condon (residues 13–15): 5'-CGAGCGAGGCCTCTATGCACGAGAGTTCCTTA GCTGCTC-3' (SEQ.ID.NO.4). The PCR and cloning steps are the same for cloning into the pLNCX2 vector.

EXAMPLE 5

Selection of Transfectants

A. Bovine Cells.

Since the pSV3neo plasmid contains the neomycin resistance gene, selective pressure was applied to transfected bovine pituitary cells using 300 µg/ml G418. Bovine pituitary cells transfected with the plasmid bearing the SV40 large T antigen (pSV3neo) outlive control cells transfected with a naive plasmid, which rarely survive beyond the sixth or seventh passage in culture. The pSV3neo transfected cells have been routinely cultured, stored cryogenically, and have been passaged up to 48 times for over a year without noticeable variations in growth patterns:

B. Human Cells.

Primary cultured human pituitary cells transfected with pSV3neo were incubated for an additional 48 to 60 hours in Gc medium with $10^{-10}$ M estradiol and nonessential amino acids before G418 selection. G418 (Sigma Chemical Co., St. Louis, Mo.) was then added at 150 µg/ml for five days and then increased to 250 µg/ml for subsequent culture. This final dose was sufficient to kill 100% of non-transfected cells. Medium was replaced every 3 to 4 days and the formation of individual colonies was monitored visually. When colonies occupied at least half of the well, we subcultured the cells into new 6-well plates in Gc media supplemented with nonessential amino acids and 0.5% fetal bovine serum and 250 µg/ml G418. The cultures were then expanded, and frozen in liquid nitrogen in medium containing 10% DMSO. Cloning was performed by diluting cells in Gc medium plus 0.5% FBS and 250 µg/ml G418 to about one cell per well in 96-well plates. Wells with more than one cell that formed colonies were not used. Clonal cell lines were then propagated, characterized as described below and frozen as above.

EXAMPLE 6

Characterization of Immortalized Cells

A. Bovine Pituitary Cell Lines.

Initial characterization of bovine pituitary cells transfected with the pSV3neo plasmid showed that these cells were immortalized. Operational immortalization was established by the survival of the various lines of immortalized bovine cells up to 48 passages. (The passage number of the various lines of immortalized bovine pituitary cells is shown below in Table 2). Non-transformed cells undergo senescence after 6 to 7 passages. Although there were minor variations in growth rates during expansion of these cultures, there was no apparent decrease in growth rate.

Also, the presence of the pSV3neo plasmid in these cell lines was demonstrated by a) survival of clones in doses of G418 (up to 4 mg/ml) lethal to wild type, non-transfected cells, and b) detection of the mRNA of the large T antigen and the neomycin resistance gene by RT-PCR of the pSV3 neo transfected cells. These results indicate the presence of the large T antigen sequence within the transfectants and suggest that immortalization is a consequence of the expression of the large T antigen.

We then tested these immortalized cells by two well-known methods to analyze malignant transformation of cells. First, cell growth in soft agar was determined (Freshney, 1987). A completely transformed cell line has reduced requirements for cell attachment and can form colonies in semi-soft agar without attachment to solid surfaces. Absence of growth in soft agar is one established criterion of a non-transformed cell line.

TABLE 2

Cell lines tested for growth in semi-soft agar.

| CELL LINE | PASSAGE NUMBER |
|---|---|
| bGH C1 | 26 |
| bGH C1+ | 26 |
| bGH C5 | 26 |
| bGH C6+ | 26 |
| bGH C3-1 | 37 |
| Tag 2 | 48 |
| Tag 2+ | 48 |
| MCF-7 w.t. (Positive control) | — |
| bp716D02 w.t. (Negative control) | 2 |

Table 2 shows cells tested for growth in soft agar (RA Freshney, 1987). The first seven cell lines listed were transfected by the pSV3neo plasmid and were tested at the passage listed. The (+) symbol after some of the cell lines indicates that the cells were cultured in 500 µg/ml G418. Wild type (w.t.) bovine pituitary cells (bp716D02) were used as a negative control and the transformed MCF-7 cells were the positive control.

The cells were diluted into soft agar at different concentrations in a six well plate as indicated in Table 3. The cells were also plated in growth medium without agar to control for viability.

TABLE 3

| Well 1: | 1000 cells/well in soft agar |
| Well 2: | 333 cells/well in soft agar |
| Well 3: | 111 cells/well in soft agar |
| Well 4: | 38 cells/well in soft agar |
| Well 5 & 6: | 6000 cells/well in DMEM/F12 5% FBS |

Cultures were maintained at 37° C. for 15 days in a humidified incubator with 5% $CO_2$. Colonies were visualized and counted only if the colony was not attached to the bottom of the plate, was spheroid and moved within the soft agar. The results are shown in Table 4.

TABLE 4

Growth of various cell lines in semisoft agar.

| Cell Line | % of control | ave % colonies/ cells plated |
|---|---|---|
| MCF-7 w.t. (Positive control) | 100 | 18.2 |
| bGH C5 | 7.7 | 1.4 |
| bGH C6+ | 0.7 | 0.13 |
| bGH C1+ | 0.3 | 0.05 |
| Tag 2 | 0.2 | 0.03 |
| bGH C1 | 0 | 0 |
| bGH C3-1 | 0 | 0 |
| Tag 2+ | 0 | 0 |
| bp716D02 w.t. (Negative control) | 0 | 0 |

Colony formation is presented as a percentage of the number of cells plated as well as a percent of the MCF-7 positive control. Four of the bovine cell lines failed to form detectable colonies, while others showed very low growth in comparison with the MCF-7 positive control. Line C5 showed 7.7% of the growth of the MCF-7 cells.

Figure 5A:
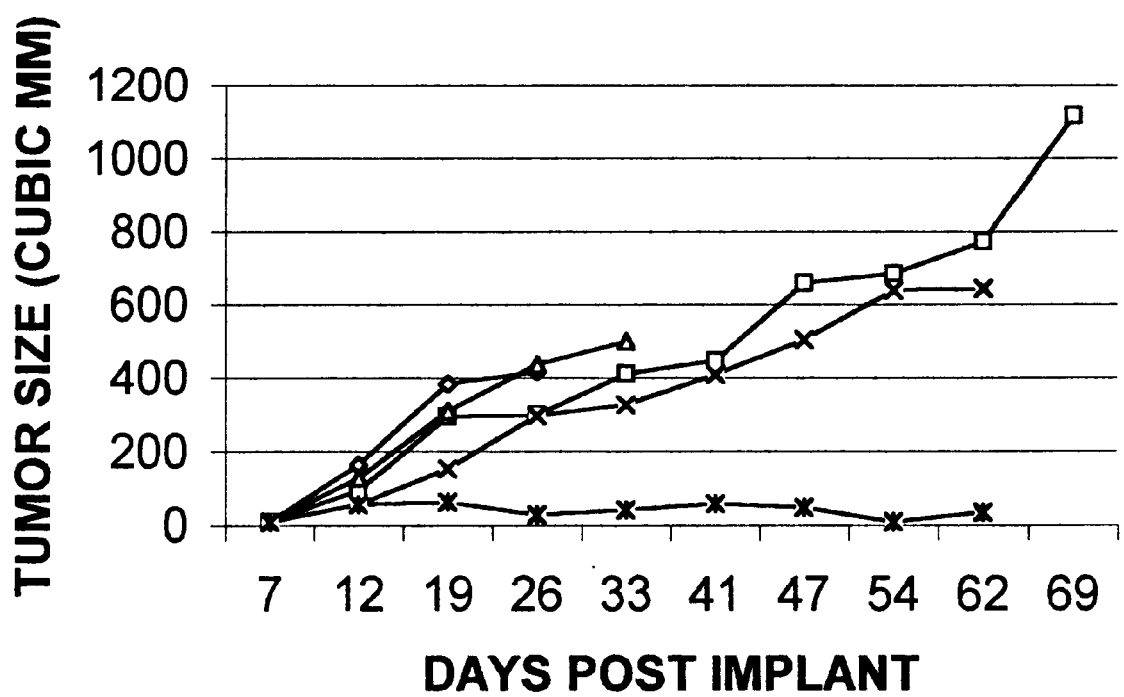
Figure 5B:
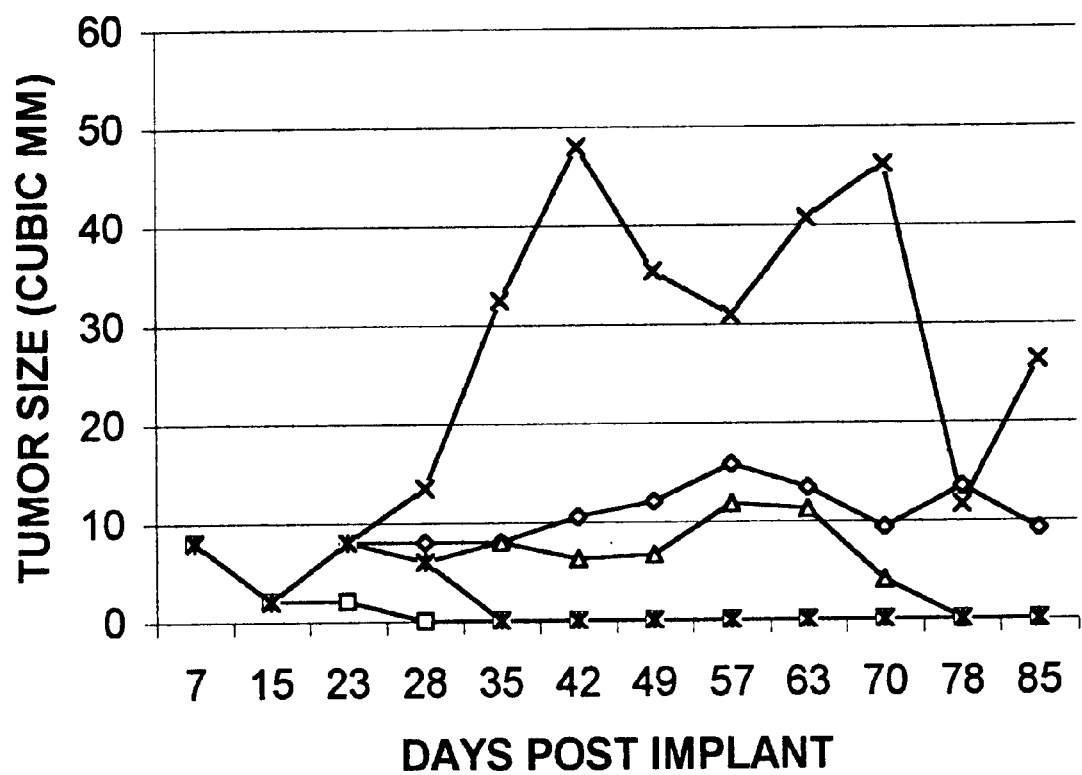
Figure 6A:
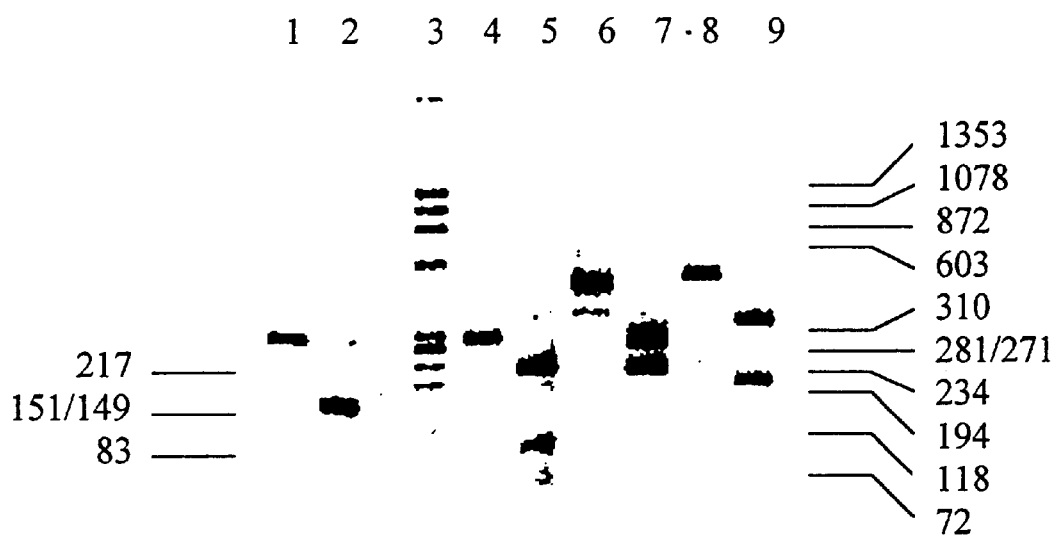
FIG. 6 shows RT-PCR of α-subunit, growth hormone, and prolactin RNA. Products of RT-PCR were analyzed on a 2% NuSieve/1% agarose gel run at 100V in 1×TAE buffer (40 mM Tris-acetate and 1 mM EDTA). (A) α-subunit product, lane 1; α-subunit product digested with XbaI, lane 2; HaeIII, φX174 marker DNA, lane 3; α-subunit product, lane 4; α-subunit product digested with HinfI, lane 5; growth hormone product, lane 6; growth hormone product digested with BanII, lane 7; prolactin product, lane8; prolactin product digested with PvuII, lane 9. (B) LTA5, α-subunit product, lane 1; LTA5 α-subunit product digested with XbaI, lane 2; LTA5 α-subunit product digested with HinfI, lane 3; HaeIII, φX174 marker DNA, lane 4; LTA6, α-subunit product, lane 5; LTA6 α-subunit product digested with XbaI, lane 6; LTA6 α-subunit product digested with HinfI, lane 7; RT-PCR reaction containing RNA for LTA5, LTA6, and LTA8 without added reverse transcriptase, lane 8; RT-PCR reaction using the cell line LnCap, lane 9; α-subunit product from primary pituitary cells, lane 10; HaeIII, φX174 marker DNA, lane 11; LTA8, α-subunit product, lane 12; LTA6 α-subunit product digested with XbaI, lane 13; LTA6 α-subunit product digested with HinfI, lane 14.

Additional studies were performed to determine if the immortalized bovine pituitary cell lines would produce tumors in athymic mice. Ten million cells were subcutaneously injected into each of five BalbC Nu Nu mice and tumor size ($mm^3$) was measured weekly for up to 90 days. We tested MCF-7 cells (ATCC, Rockville, Md.) as a positive control and the immortalized bovine pituitary cell lines, C3-1 and C1+. Mice injected with MCF-7 cells showed progressive tumor growth until reaching a mass which was fatal, about 600 $mm^3$ or less (FIG. 6A). (Mice represented by ◇ or △ died at 26 and 33 days respectively.) This indicates that the transformed MCF-7 cells rapidly proliferate in athymic mice. However, the results obtained with the bovine cell lines C1+ (FIG. 5B) and C3-1 (FIG. 5C) showed an absence of progressive tumor growth with most mice showing no detectable tumors. Three out of 10 mice did exhibit measurable tumors at about 30 days post implant, but these tumors were only 10% or less of the size of the MCF-7 tumors and regressed to zero (2 mice) or minimal (1 mouse) volume at 90 days post implantation. The Y axis scales on FIGS. 5 A, B and C are different. The results of the soft agar and nude mouse studies indicate that the immortalized bovine pituitary cells exhibit two characteristics of non-transformed cells: absence of growth in soft agar and inability to form tumors in athymic mice.

The immortalized bovine pituitary cell lines were then characterized by immunohisto-chemical staining specific for particular types of cells. Bovine cultures were grown in chamber slides (Nalgene Nunc, Inc., Naperville, Ill.) until approximately 50% confluent and were rinsed 3 times with PBS. For the pituitary hormone stains, cells were fixed with Zamboni fixative (Hatfield, J M and Hymer, W C, 1985) for 20 minutes at room temperature. For staining of intermediate filaments, cells were fixed in 70% methanol/30% acetone at −20° C. for 10 seconds. After fixation, cells were rinsed twice in PBS. Nonspecific binding was blocked by incubating in PBS with 5% goat serum and 0.1% sodium azide for 20 minutes in a humidified incubator at 37° C. After rinsing three times in PBS, each chamber received approximately 2 $\mu$g/ml of the appropriate primary antibody: 1) rabbit anti-goat polyclonal Ig, a nonspecific control (Sigma Chemical Co., Catalog No. B-7014), 2) rabbit anti-bovine growth hormone (Biogenesis, Inc., Catalog No 4750–0959), 3) rabbit anti-bovine FSH (Biogenesis, Inc., Catalog No. A558/R4H), 4) Mouse nonspecific $IgG_1$ (Dako Corp., Catalog No. X-0931), 5) mouse anti-vimentin monoclonal $IgG_1$, (Sigma Chemical Co, Clone No. V-9), 6) mouse anti-cytokeratin pan AEI/AE3 monoclonals (Dako Corp., Catalog No. M-3515). Cells were incubated for 30 minutes at 37° C. with the primary antibodies and were washed three times in PBS.

The secondary antibodies were applied at a 1:500 dilution in PBS, 1% BSA and included: peroxidase-conjugated goat anti-mouse IgG (Jackson Laboratories, Catalog No. 115-035-062) or peroxidase-conjugated donkey anti-rabbit IgG (Jackson Laboratories, Catalog No. 711-035-152). Cells were incubated for 30 minutes at 37° and washed four times in PBS with 1% BSA. Cells were then reacted in 667 mg/ml diaminobenzidine (Sigma Chemical Co., St. Louis, Mo.) with a 1:1000 dilution of 30% hydrogen peroxide. This reaction was stopped after 10–20 minutes by rinsing four times in deionized water. Slides were counterstained with hematoxylin and preserved using an aqueous permanent mounting medium, Ultramount (Dako Corp., Carpinteria, Calif.)

The results of the immunohistochemical staining showed that all bovine cultures were strongly positive for vimentin, a common feature of immortalized and transformed cells, as well as normal fibroblasts. While the original bovine primary cultures showed strong staining for the epithelial cytokeratins in approximately 2% of the cells, more uniform staining was detected in clones C3, C6 and Tag2. We were unable to detect GH or FSH by immunostaining. However, the limited sensitivity of the immunostaining methods may preclude our ability to detect low levels of expression.

Additional experiments were performed using highly sensitive immunological methods to detect bovine growth hormone within live, individual cells in the immortalized cultures. Bovine GH-specific monoclonal antibodies were obtained from Biogenesis, Inc. (Catalog No. 4750–0939) and OEM Concepts (Toms River, N.J.). The specific sensitivity and specificity of these antibodies was confirmed as follows: An immunoblot assay procedure showed a visibly linear response to commercial bovine GH (Biogenesis, Inc., Sandown, N.H.) from 10 to 100 ng/100 uL. Western blots of commercial preparations of purified bovine GH and bovine pituitary extracts showed reactivity of a single band at the molecular size of bovine GH. A cellular blotting method was used to monitor bovine GH secretion from pituitary cells grown in culture, as described by Gibson-D'Ambrosio, et al. (1995). By localizing bovine GH within cultures, it was possible to obtain enriched cultures of bovine somatotropes prior to transfection with pSV3neo. Subsequent generations of these transfected clones showed enrichment of the proportion of cells secreting bovine GH. These cell lines are indicated in Table 2 with the designation bGH, e.g., bGH C5. However, the enriched bovine GH cultures also contained cells that do not appear to secrete bovine GH, indicating that the surviving cells are heterogeneous.

Immunoblots showed a positive signal from FBS-containing media probably due to bovine GH in FBS since non-FBS containing media was negative. To test for secretion of bovine GH from immortalized bovine cell line, cultures of passage 2–10 were grown to confluence in FBS-containing media, washed three times with PBS and incubated for 3 hours in media without FBS. Duplicate wells contained 10 $\mu$M bovine growth hormone releasing factor (GHRF). The results showed that the conditioned media contained detectable levels of bovine GH and the amount secreted appeared to be potentiated by exposure of the cultures to GHRF. These results suggest that cultures of immortalized bovine pituitary cells secrete bovine GH into the culture medium.

Further analysis was performed to determine the presence of bovine GH within these cultures. A Western blot procedure according to the method of Fernandez and Kopchick (1990) was performed using a polyclonal antibody to bovine GH (Biogenesis, Inc., Catalog No. 4750-0959). The results showed a band at the approximate molecular weight of bovine GH in the extracts of cell lines C5, C6, Tag1 and Tag2 as well as early passage wild-type cells. However, several other resolvable bands were also immunoreactive, possibly due to cross-reaction of the primary polyclonal antibody. RT-PCR was used to determine if the GH mRNA could be detected within the immortalized bovine pituitary cells. Using primers to exon I and exon 4, we were able to detect amplification of a correctly-sized DNA in cell lines C1, C5 and C6 at the sixth passage. This signal was also detected in low passage primary cultures and digestion of the RT-PCR product with SmaI yielded two bands of the predicted size.

In summary, the characterization of bovine pituitary cells immortalized by transfection with the pSV3neo plasmid shows that the resulting cell lines were immortal and contained the pSV3neo plasmid which probably induced immortalization through expression of the large T antigen. The immortalized bovine pituitary cells appear non-transformed by two commonly used methods to assess cellular transformation, growth in semi-soft agar and athymic mice. By immunohisto-chemical staining, the co-expression of the cytokeratins and vimentin in several cell lines suggests that epithelial cells have been immortalized by transfection with the pSV3neo plasmid. The RT-PCR results indicate that these cultures express the mRNA for large T antigen and bovine growth hormone. Additional immunological analyses by different monoclonal and polyclonal antibodies show the presence of bovine growth hormone and preliminary results suggest that it is secreted. Taken together the results strongly suggest the presence of immortalized bovine somatotropes within these cultures.

B. Human Pituitary Cell Lines.

Three different cell lines were isolated from transfection experiments described above. These are shown below with passage number:

TABLE 5

Cell lines tested for growth in semi-soft agar.

| CELL LINE | PASSAGE NUMBER |
|---|---|
| Human LTA5/pSV3neo | 18 |
| Human LTA6/pSV3neo | 24 |
| Human LTA8/pSV3neo | 21 |

Since these cell lines have been passaged well beyond the point where primary human pituitary cultures die (pass 4–5), this is evidence for an immortalized state for each cell line. We initially characterized these cells by determining the expression of the large T antigen mRNA within these immortalized clones. We isolated total RNA from LTA5, LTA6 and LTA8 cell lines by well-known methods in the art. This RNA was then used to perform RT-PCR using primers specific for the 5' and 3' ends of the entire large T antigen sequence. The primers were: the 5' primer, 5'-GCAGCTAATGGACCTTCTAGGTC-3' (SEQ.ID.NO.5) and the 3' primer, 5'-GTCAGCAGTAGCCTCATCATCAC-3' (SEQ.ID.NO.6). Reverse transcription was performed using random hexamers under the following conditions: the reaction mixture contained 50 mM Tris-HCl (pH 8.3), 75 mM KCl, 3mM $MgCl_2$, 10 mM DTT, 1 mM dNTPs, 1 unit/$\mu$l RNAsin (Promega, Catalog No. N2111), 2.5 $\mu$M random hexamers (Promega, Catalog No. C 1181), 2 units/$\mu$l Moloney Murine Leukemia Virus reverse transcriptase (Promega, Catalog No. M1701, and 12.5 ng/$\mu$l of RNA from the immortalized pituitary cell lines were incubated at 22° C. for 15 minutes then moved to 42° C. for 45 minutes. The samples were then heated for 5 minutes at 95° C. and then stored on ice. A 5 $\mu$l volume was then removed from the reverse transcription reaction and mixed in a 25 $\mu$l PCR reaction containing 1 $\mu$M 5' and 3' large T antigen primers, 4 units of Taq DNA polymerase (Promega, Catalog No. M1665), 10 mM Tris-HCl (pH 9), 50 mM KCl, 0.1% Trition X-100, and 1.5 mM $MgCl_2$. No additional dNTPs were added to the reaction with the final contribution from adding 5 $\mu$l of the RT reaction being 0.2 mM. The reactions were incubated initially for 5 minutes at 95° C. and then incubated for thirty cycles of 95° C. for 1 minute, 64° C. for 1 minute, and 72° C. for 1 minute. The resulting RT-PCR products were then analyzed by agarose gel electrophoresis.

The products from all three reactions contained three dominant bands for large T antigen but varied in predominance depending on the RNA used in the RT-PCR. For LTA5, the predominant product was the predicted 670 bp band with much less intense bands at 500 bp and 320 bp. For LTA 6 and LTA8, the 320 bp band was much more intense than the larger bands. This result suggested that different forms of large T antigen were present in each cell line possibly due to alternate splicing (Eul, J, et.al., 1996). Using the products generated in the RT-PCR reactions, restriction enzyme analysis was used to map the large T antigen sequence present in each cell line. Restriction enzymes were chosen that span the entire length of the intact large T antigen sequence. These were: SspI at 44 bp, Rsa I at 142 and 253 bp, NdeI at 290 bp, TaqI at 390 bp, AluI at 486 bp, HinfI at 536 and 560 bp, and BfaI at 646 bp. The 670 bp band from the LTA5 RT-PCR product was cut by all the restriction enzymes except BfaI at 646 bp. Therefore, the LTA5 contained large T antigen with coding sequences at least through 560 bp. The resulting restriction products from LTA6 and LTA8 showed that they both contain smaller forms of the large T antigen sequence. Ndel at 290 bp, TaqI at 390 bp, or AluI at 486 bp did not cut the smaller species of T antigen. Both of the smaller bands were cut by HinfI however. These results suggest that LTA6 and LTA8 contain primarily a form of large T antigen that were deleted for the middle portion of the sequence beyond 253 bp through ~500 bp. This is not surprising since the large T antigen can undergo alternate splicing of exons 1 and 2 to yield different forms of the antigen but still immortalize cells with only the amino terminus required (Asselin, C and Bastin, M, 1985).

These cell lines were also characterized with respect to their growth in soft agar as described previously in the characterization of the immortalized bovine pituitary cells. Cell lines transfected by the pSV3neo plasmid and surviving senescence were compared to primary human pituitary cells and tumorigenic wild type MCF-7 cells.

The cells were diluted in soft agar as shown in Table 6. Cells were also plated in Gc medium +NEAA to control for viability.

TABLE 6

| Well 1: | 1000 cells/well in soft agar |
|---|---|
| Well 2: | 333 cells/well in soft agar |
| Well 3: | 111 cells/well in soft agar |
| Well 4: | 38 cells/well in soft agar |
| Well 5 & 6: | 6000 cells/well of human primary pituitary culture hp991112, pass 2. |

Table 7 summarizes the results at the highest concentration of cells plated and compares them to the results obtained with MCF-7 cells.

TABLE 7

Growth of Human Pituitary Cell Lines in semisoft agar.

| Cell Line | % of control | avg % colonies/cells plated |
|---|---|---|
| MCF-7 w.t. (Positive control) | 100 | 72 |
| Human LTA5(18)/pSV3neo | 0 | 0 |
| Human LTA6(24)/pSV3neo | 0.035 | 0.025 |
| Human LTA8(21)/pSV3neo | 12.6 | 9.1 |
| hp991112(2) | 0 | 0 |

The pSV3neo transfected cell lines LTA5 and LTA6 are probably non-transformed cell types by their lack of growth in semisoft agar. The LTA8 cell line showed a slight ability to grow in semisoft agar but may also be immortalized.

Human pituitary cells were prepared for immunohistochemical staining by the same methods that were previously described for bovine cells. Since the vimentin and cytokeratin antibodies were not species-specific, the same monoclonal antibodies were utilized for human and bovine staining. The following human-specific antibodies were also used: 1) Mouse anti-human E-cadherin monoclonal IgG, (Clone HECD-1, Zymed Laboratories, San Francisco, Calif.), 2) mouse anti-GH monoclonal IgG$_1$ (Biogenesis, Inc., Catalog No., 4750–0280), 3) mouse anti-human FSH alpha subunit IgG$_1$ (Clone MAB111, AbProbe International, Portland, Me.).

The results are summarized in Table 8 and include staining of both primary cultures and immortalized cell lines. Strong staining for GH, FSH and cytokeratins was apparent within heterogeneous colonies of the primary cultured pituitary cells. Vimentin staining was rare in the primary cultures, suggesting minimal contamination by fibroblasts. This confirms that the panning method is effective in removal of fibroblasts from these cultures. Although GH and FSH could not be detected in the pSV3neo transfectants, two of the clones expressed markers of an epithelial phenotype. LTA8 expressed both E-cadherin and cytokeratin and LTA6 expressed only the cytokeratins. LTA5 expressed neither epithelial marker. As with the bovine cell lines, the expression of vimentin was ubiquitous after immortalization. However, the expression of epithelial markers suggests that we have immortalized human epithelial cells, which may include endocrine cells, follicular stellate cells or endothelial cells. The immortalized cell lines were further characterized by RT-PCR analysis of the messenger RNA of common pituitary hormones.

TABLE 8

Immunostaining of Human Fetal Pituitary Cultures

| Cells | E-Cadherin | Cyto-keratins | Vimentin | GH | FSH |
|---|---|---|---|---|---|
| HP990821 (primary) | + | + | + | + | ? |
| HP990902 (primary) | + | + | + | + | − |
| HP990923 (primary) | + | + | + | + | + |
| LTA5 (immortalized) | − | − | + | − | − |
| LTA6 (immortalized) | − | + | + | − | − |
| LTA8 (immortalized) | + | + | + | − | − |

Figure 6B:
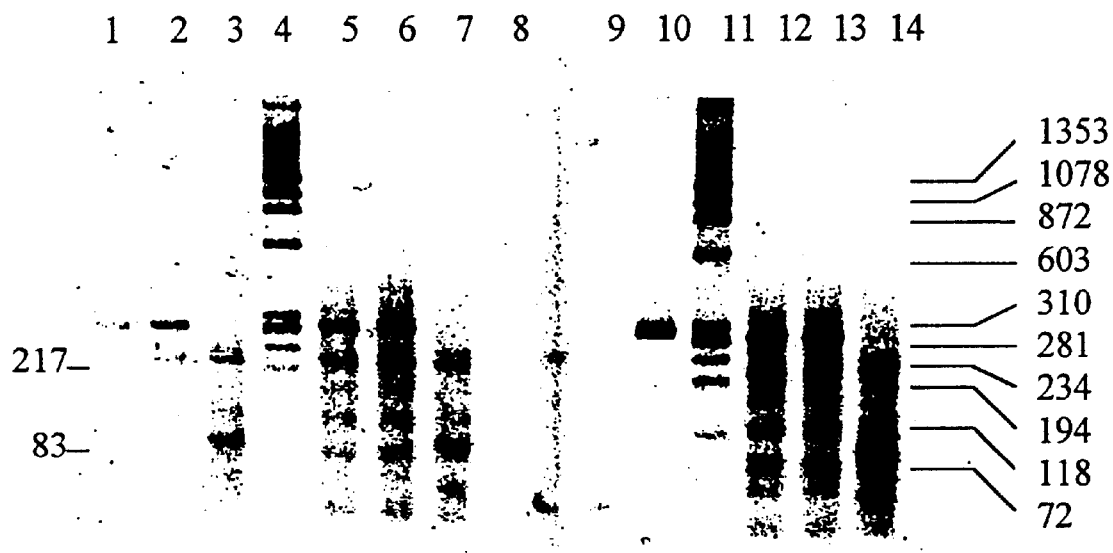

Total RNA was isolated from LTA5, LTA6, and LTA8 pituitary cell lines using methods well-documented in the art. These RNAs were then analyzed by RT-PCR for the presence of messages for the pituitary hormone α-subunit, growth hormone, and prolactin. The α-subunit is common to FSH, TSH and LH. Cells dispersed for primary pituitary cultures were used as controls for the presence of all three mRNAs. RT-PCR was performed as described above with specific primers to α-subunit, growth hormone, and prolactin. The following primers were used for the PCR portion of the analysis: α-subunit 5' primer, 5'-GCAGCTATCTTTCTGGTCACATTG-3' (SEQ.ID.NO.7) and 3' primer, 5'-GTGGCACGCCGTGTG-3' (SEQ.ID.NO.8); growth hormone 5' primer, 5'-CTGGCTTCAAGAGGGCAG-3' (SEQ.ID.NO.9) and 3' primer, 5'-CGTAGTTCTTGAGCAGTGCGT-3' (SEQ.ID.NO.10). The reactions were first incubated for 5 minutes at 95° C. and then incubated for forty cycles of 95° C. for 1 minute, 55° C. for 1 minute, and 72° C. for 1 minute. The resulting RT-PCR products were then analyzed by agarose gel electrophoresis (see FIG. 6A). The RT-PCR products obtained from primary pituitary RNA contained a 300 bp band for α-subunit, a 503 bp band for growth hormone, and a 557 bp band for prolactin. The α-subunit product was fully digested with XbaI to give 151 and 149 bp products and with HinfI to yield a 217 and 83 bp products. Growth hormone was digested with BanII to yield 215 and 288 bp products and prolactin cleaved by PvuII generated 196 and 361 bp products. RT-PCR of LTA5, LTA6, and LTA8 RNA gave no specific products corresponding to those found for growth hormone and prolactin from primary pituitary cells. There were specific products generated from RT-PCR using primers specific for α-subunit at ~300 bp (see FIG. 6B). The RT-PCR product for LTA8 appears to be slightly smaller than that generated from the primary pituitary cells. When the resulting products for all three cell lines were digested with XbaI and HinfI, all are cleaved by HinfI suggesting the sequences were from α-subunit. However, there was no digestion of the products with XbaI. Because the primary pituitary cells are of different origin than the cells used for immortalization, there may be a mutation present in the pituitary used to generate the cell lines. Alternate splicing of the first intron is also known to result in restriction length polymorphisms (Fiddes, J C and Goodman, H M,1981). This may account for the difference in size observed between the LTA8 and primary pituitary cell RT-PCR products. Other nonspecific bands are also present as a consequence of increasing the number of PCR cycles from 30 to 40. These bands were also present when RT-PCR was performed on primary pituitary cell RNA using 40 PCR cycles.

In summary, human pituitary cells were immortalized by transfection with the pSV3neo plasmid and these cells appear to be non-transformed by their lack of growth in soft agar. Some of these cells appear to be epithelial by immunohistochemical staining for E-cadherin and cytokeratins. RT-PCR analysis showed a lack of the mRNA for prolactin or growth hormone. However, the α-subunit mRNA was apparently present, but this mRNA may be mutated at the site required for digestion by XbaI. These cultures also did not secrete detectable levels of FSH, LH or TSH, suggesting that large T antigen expression may interfere with the expression of human pituitary hormones.

REFERENCES

Adams, J M and Cory, S, Science 281: 1322–1326, 1998.
Alarid, E T, Windle, J J, Whyte, D B, and Mellon, P L, Development 122: 3319–3329, 1996.
Arey, B J, Stevis, P E, Deecher, D C, Shen, E S, Frail, ED, Negro-Vilar, A and Lopex, F J, Molecular Endocrinology 11: 517–526, 1997.

Asselin, C and Bastin, M, Journal of Virology, 56: 958–968, 1985.

Alitalo, K, Bishop, J M, Smith, D H, Chen, E Y, Colby, W W, and Levinson, A D, Proceedings of the National Academy of Sciences 80: 100–104, 1983.

Ausubel, F M, Brent, R, Kingdom, R E, Moore, D M, Seidman, J D, Smith, J A and Struhl, K, *Current Protocols in Molecular Biology*, Green Publishing Associates, Inc. & John Wiley & Sons, Inc., N.Y.

Barlier, A, Pellegrini-Bouiller, I, Caccavelli, L, Gunz, G, Morange-Ramos, I, Jaquet, P, and Enjalbert, A, Hormone Research 47: 227–234, 1997.

Bedford, F K, Christopherson, K, Nachtigal, M W, Shen, W H, Julius, D J and Ingraham, HA, Hormone Research 45 (Suppl 1): 19–21, 1996.

Bernard, O., Reid, H. H. and Bartlet, P. F., J. Neurosci. Res. 24:9–20, 1989.

Berthon, P, Goubin, G, Dutrillaux, B, Degeorges, A, Faille, A, Gespach, C and Calvo, F, International Journal of Cancer 52: 92–97, 1992.

Blasi, E., Radzioch, D., Durum, S. K., and Varesio, L., Eur. J. Immunol. 17: 1491–1498, 1987.

Briers, T. W., Desmarettz, D. and Vanmechelen, E., Neuroimmunol. 52: 153–164, 1994.

Briers, T. W., De Voorde, A. V. and Vanderstichele, H., In Vitro Cell. Dev. Biol. 29A: 847–854, 1993.

Caciceodo, L, Pohl, S L, and Reichlin, S, Endocrinology 108: 1012–1019, 1981.

Cai, W Y, Alexander, J M, Hedley-White, E T, Scheithauer, B W, Jameson, J L, Zervas, N T and Klibanski, A, Journal of Clinical Endocrinolgoy and Metabolism 78: 89–93, 1994.

Chakrabarti, R, Srivatsan, E S, Wood, T F, Eubanks, P J, Ebrahimi, S A, Gatti, R A, Passaro, E and Sawicki, M P, Genes, Chromosomes and Cancer 22:130–137, 1998.

Chomczynski, P, Brar, A and Frohman, L A, Endocrinology 123: 2276–2283, 1988.

Chou, J Y, Molecular Endocrinology 3: 1511–1514, 1989.

Coffin, J M and Varmus, H E, *Retroviruses*, Cold Spring Harbor Laboratory Press, NY.

Coleman, T A, Chomczynski, P, Frohman, L A and Kopchick, J J, Molecular and Cellular Endocrinology 75: 91–100, 1991.

Condliffe, P G, Mochizuki, M, Fontaine, Y A and Bates, R W, Endocrinology 85: 453–464, 1969.

Cook, N E, Coit, D, Shine, J, Baxter, J D, Martial, J A, Journal of Biological Chemistry 256: 4007–4016,1981.

Dale, T C, Biochemistry Journal 329: 209–223, 1998.

De Leeuw, R, Mulders, J, Voortman, G, Rombout, F, Damm, J and Kloosterboer, L, Molecular Human Reproduction 2: 361–369, 1996.

Ericson, J, Norlin, S, Jessell, T M and Edlund, T, Development 125: 1005–1015, 1998.

Eul, J, Graessmann, M, and Graessmann, A, Nucleic Acids Research, 24: 1653–1661, 1996.

Facchini, L M and Penn, L Z, FASEB Journal 12: 633–651, 1998.

Fernandez, E and Kopchick, J J, Analytical Biochemistry 191: 268–271, 1990.

Fiddes, J C and Goodman, H M, Journal of Molecular and Applied Genetics 1: 3–18, 1981.

Filmus, J, Remani, J and Klein, M H, Nucleic Acid Research 20: 2755–2769, 1992.

Flaws, J A and Suter, D E, Biology of Reproduction 48: 1026–1035, 1993.

Freshney, IR, *Culture of animal cells: A manual of basic technique*. Wiley-Liss, New York, 1987.

Furth, J, Recent Progress in Hormone Research 11: 221–257, 1955.

Galway, A B, Hsueh, A J W, Keene, J L, Yamoto, M, Fauser, B C J M, and Boime, 1, Endocrinology 127:93–100, 1990.

Gibson-D'Ambrosio, R E, Brady, T, and D'Ambrosio, S M, Biotechniques 19: 784–790, 1995.

Gluzman, Y, Frisque, R J, and Sambrook, J, Cold Spring Harbor Symposium on Quantitative Biology 44: 293–300, 1980.

Gonsky, R, Herman, V, Melmed, S and Fagin, J, Molecular Endocrinology 5: 1687–1695, 1991.

Guillemin, R, Science 202:390–402, 1978.

Ham, J, Webster, J, Baond, J A, Jansani, B, Lewis, M D, Hepburn, P J, Davies, J S, Lewis, B M, Thomas, D W, Scanlon, M F, Journal of Clinical Endocrinology and Metabolism 83: 1598–1603, 1998.

Hansen, C B, Kao, G Y, Hoase, E H, Salipsky, S and Allen, T M, Biochimica and Biophysica Acta 1239: 133–144, 1995.

Hatfield, J M and Hymer, W C, Cytometry 6: 137–142, 1985.

He, TC, Sparks, A B, Rago, C, Hermeking, H, Zawel, L, de Costa, L T, Morin, P J, Vogelstein, B, and Kinzler, K W, Science 281: 1509–1512, 1998.

Health, T D and Martin, F J, Chemistry and Physics of Lipids 40: 347–358, 1986.

Hedlund, T E and Miller, G J, The Prostate 24:221–228, 1994.

Hedlund, T E, Duke, R C, Schleicher, M S, Miller, G J, The Prostate 36: 92–101, 1998.

Hodson, C A, Prolactin, I N: *Handbook of Endocrinology*, Gass, G H and Kaplan, H M, eds, 1996.

Hoeben, E., Briers, T., Vanderstichele, H., DeSmet, W., Heyns, W., Deboeal, L., Vanderhoydonck, R., and Verhoeven, G., Endocrinol. 136: 2862–2873, 1995.

Ishida, T, Ando, H, Nomura, S, Ishikawa, K, Kurauchi, O, Mizutani, S, Kobayashi, M, Eguchi, G and Toado, Y, Proceedings of the Society for Experimental Biology and Medicine 209: 251–256, 1995.

Kashio, Y, Chomczynski, P, Downs, T R, Frohman, L A, Endocrinology 127: 1129–1135, 1990.

Katayama, T, Shiota, K and Takahasi, M, Molecular and Cellular Endocrinology 69: 179–185, 1990.

Keene, J L, Matzuk, M M, Otani, T, Fauser, B C J M, Galway, A B, Hsueh, A J W and Boime, I, The Journal of Biological Chemistry 264: 4769–4775, 1989.

Kelly, E J, Sandgren, E P, Brinster, R L, Palmiter, R D, Proceedings of the National Academy of Sciences 94: 10045–10050, 1997.

Land, H, Parada, L F, Weinberg, R A, Nature 304: 596–602, 1983.

Lechner, M S and Laimins, L A, Virology 185:563–571, 1991.

Leon, S P, Carroll, R S, Dashner, K, Glowacka, D, Black, P M, Journal of Clinical Endocrinology and Metabolism 79: 51–55, 1994.

Lie, B L, Leung, E, Leung, P C K, and Auersperg, N, Molecular and Cellular Endocrinology 120: 169–176, 1996.

Madsen, M. W., Lykkesfeldt, A. E., Laursen, I., Nielsen, K. V. and Briand, P., Cancer Res. 52: 1210–1217, 1992.

Mellon, P L, Windle, J J and Weiner, R I, Recent Progress in Hormone Research 47: 69–96, 1991.

Nagpal, M I, Wang, e, Calkins, J H, and Lin, T, Cell and Tissue Research 275: 459–465, 1994.

O'Guin, W M, Schermer, A, Lynch, M and Sun, T, IN: *Cellular and Molecular Biolopy of Intermediate Fila-* ments. Goldman, R D and Steinert, P M, eds, Plenum Press, New York, Pgs. 301–334, 1990.

Paris, N, Rentier-Delrue, F, Defontaine, A, Goffin, V, Lebrun, J J, Mercier, L, and Martial, J A, Biotechnology and Applied Biochemistry 12: 436–449, 1990.

Pulverer, B J, Fisher, C, Vousden, K, Littlewood, T, Evan, G and Woodgett, J R, Oncogene 9: 59–70, 1994.

Raymon, H K, Thode, S, Zhou, J, Friedman, G C, Pardinas, J R, Barrere, C, Johnson, R M, and Sah, D W, Journal of Neuroscience 19: 5420–5428, 1999.

Reddy, V B, Beck, A K, Garramone, A J, Vellucci, V, Lustbader, J and Berstine, E G, Proceeding of the National Academy of Sciences 82: 3644–3648, 1985.

Sanno N, Teramoto, A, Sugiyama, M, Matsuno, A, Takumi, I, Tahara, S and Osamura, R Y, Hormone Research 50: 11–17, 1998.

Schwendener, R A, Trub, T, Schott, H, Langhals, H, Barth, R F, Groscurth, P and Hengartner, H, Biochimica and Biophysica Acta 1026: 69–79, 1990.

Simmons, D M, Voss, J W, Ingraham, H A, Holloway, J M, Broide, R S, Rosenfeld, MG and Swanson, L W, Genes and Development 4: 695–711, 1990.

Simon, J A, Danforth, D R, Hutchison, J S, Hodgen, G D, Journal of the American Association of Medicine 259:3290–3295, 1988.

Sinha, Y N, Endocrine Reviews 16: 354–369, 1995.

Stein, G H, Journal of Cell Physiology 125: 36–44, 1985.

Strom, S. C., Faust, J. B., Cappelluti, E., Harris. R. B., and Lalwini, N. D. Digest. Dis. and Sci., 36: 642–652, 1991.

Soule, H D, Vazquez, J, Long, A, Albert, A and Brennan, M, Journal of the National Cancer Institute 51: 1409–1416, 1973.

Southern, P J and Berg, P J, Journal of Molecular and Applied Genetics 1: 327–341, 1982.

Szkudlinski, M W, Grossmann, M and Weintraub, B D, Trends in Endocrinology and Metabolism 7: 277–286, 1996.

Tavassoli, M. and Shall, S. Oncogene 2: 337–345, 1988.

Uyttersprot, N., Costagliola, S., and Miot, F., Mol Cell Endocrinol, July 25;142(1–2):35–9.

Valenti, S., Sarkissian, A, Giusti, M, Giordano, G, and Dahl, K D, Journal of Neuroendocrinology 7: 673–679, 1995.

Vanderstichele, H., Delaney, B., De Winter, J., De Jong, F., Rombauts, L., Verhoeven, G., Dello, C., De Voorde, A. V., and Brier, T., Biol. Reprod. 50: 1190–1202, 1994.

Wang, Q, Maher, V M and McCormick, J J, Gene 119:155–161, 1992.

Windle, J J, Weiner, R I, and Mellon, P L, Molecular Endocrinology 4: 597–603, 1990.

Wood, W M, Kao, M Y, Gordon, D F and Ridgeway, E C, The Journal of Biological Chemistry 264: 14840–14847, 1989.

Zhang, X, Horwitz, G A, Prezant, T R, Valentini, A, Nakashima, M, Bronstein, M D and Melmed, S, Molecular Endocrinology 13: 156–166, 1999.

While various embodiments of the present invention have been described in detail, it is apparent that modifications and adaptations of those embodiments will occur to those skilled in the art. It is to be expressly understood, however, that such modifications and adaptations are with the scope of the present invention and are only limited by the following claims.

What is claimed is:

1. A method of immortalizing non-transforrned cells comprising the steps of:
   (a) obtaining a primary culture of cells;
   (b) transfecting said primary cells with a vector containing a foreign gene to produce transfected, immortalized cells that are not transformed; and
   (c) isolating said transfected cells from non-transfected cells to obtain a culture of immortalized cells, wherein said immortalized cells are pituitary cells or follicular stellate cells.

2. The method of claim 1, wherein said primary cells are transfected by cationic liposomes, retroviruses or immuno-liposomes.

3. The method of claim 1, wherein said primary cells are transfected by immunoliposomes.

4. The method of claim 1, wherein said primary cells are hormone-producing cells.

5. The method of claim 1, wherein said primary cells are isolated with immobilized antibody specific for a hormone or peptide hormone receptor expressed by pituitary cells prior to transfection.

6. The method of claim 1, wherein said primary cells are cultured with an extracellular matrix protein.

7. The method of claim 6, wherein said exracellular matrix protein is fetuin, matrix, or disrupted MCF-7 cells.

8. The method of claim 6, wherein said extracellular matrix protein is fetuin.

9. The method of claim 1, wherein said primary cells are pituitary cells.

10. The method of claim 9, wherein said pituitary cells are lactotropes, somatotropes, thyrotropes, gonadotropes, corticotropes or melanotropes.

11. The method of claim 1, wherein said primary cells are human cells.

12. The method of claim 1, further comprising culturing said primary cells with at least one environmental factor to control proliferation or differentiation prior to or after transfection.

13. The method of claim 12, wherein said environmental factor is a growth factor or other factor controlling the expression of the foreign gene.

14. The method of claim 13, wherein said growth factor is activin, tri-iodothyronine, galinin, nerve growth factor, leukemia inhibitory factor, hepatocyte growth factor, acidic or basic fibroblast growth factor, platelet-derived growth factor, pituitary adenylate cyclase-activating polypeptide, vasopressin, retinoic acid, vasoactive intestinal polypeptide or gonadotropin releasing hormone (GnRH).

15. The method of claim 1, wherein said vector is a retroviral expression vector.

16. The method of claim 15, wherein said retroviral expression vector is pLNCX2 or pLXSN.

17. The method of claim 16, wherein said retroviral expression vector contains an inducible promoter.

18. The method of claim 17, wherein said inducible promoter is derived from beta galactosidase, T7, mouse metallothionein, glucocorticoid or tetracycline response elements.

19. The method of claim 1, wherein said foreign gene is an establishment oncogene.

20. The method of claim 19, wherein said establishment oncogene is a viral oncogene, a cellular proto-oncogene, a tumor suppressor gene or a derivative thereof.

21. The method of claim 20, wherein said viral oncogene is large T antigen of SV40, an oncogene from the Epstein-Barr virus, or E7 gene of human papilloma virus.

22. The method of claim 21, wherein said viral oncogene is large T antigen of SV40.

23. The method of claim 20, wherein said cellular proto-oncogene is gsp, gip2, myc, fos or pituitary tumor-transforming gene.

24. The method of claim 20, wherein said cellular proto-oncogene is myc.

25. The method of claim 1, further comprising transfecting said primary cells with an anti-apoptosis gene.

26. The method of claim 25, wherein said anti-apoptosis gene is a Bcl2 gene.

27. The method of claim 1, wherein said immortalized cells remain viable at least at a 5-fold greater passage number than senescence of non-immortalized primary cells under similar culture conditions.

28. An immortalized cell line produced by the method of claim 1.

29. The immortalized cell line of claim 28, wherein said immortalized cell line is a follicular stellate cell line.

30. The immortalized cell line of claim 28, wherein said immortaliedcell line is a pituitarcell line.

31. The immortalized cell line of claim 28, wherein said immortalized cell line is cultured in media free of other cell lines.

32. The immortalized cell line of claim 30, wherein said immortalized cell line produces prolactin, growth hormone, luteinizing hormone, follicle-stimulating hormone, thyroid-stimulating hormone, adrenocorticotropic hormone or melanocyte-stimulating hormone.

33. The method of claim 24, wherein said myc gene is contained within a vector that comprises an inducible promoter.

34. The method of claim 33, wherein said inducible promoter is derived from beta galactosidase, T7, mouse metallothionein, glucocorticoid or tetracycline response elements.

35. The method of claim 1, wherein said vector comprises an inducible promoter.

36. The method of claim 35, wherein said inducible promoter is derived from beta galactosidase, T7, mouse metallothionein, glucocorticoid or tetracycline response elements.

37. The method of claim 1, wherein said vector comprises endogenous promoter sequences specific to normal pituitary cell expression.

38. The method of claim 37, wherein said promoter sequences are pituitary hormone promoter sequences or the thereof.

* * * * *

UNITED STATES PATENT AND TRADEMARK OFFICE
CERTIFICATE OF CORRECTION

PATENT NO.   : 6,458,593 B1
DATED        : October 1, 2002
INVENTOR(S)  : Musick et al.

It is certified that error appears in the above-identified patent and that said Letters Patent is hereby corrected as shown below:

Column 35,
Line 50, delete "exracellular" and insert -- extracellular -- therefor;
Line 51, after "fetuin," and before "matrix" insert -- matrigel basement membrane --;

Column 37,
Line 4, delete "immortaliedcell" and insert -- immortalized cell -- therefor;
Line 4, delete "pituitarcell" and insert -- pituitary cell -- therefor;

Column 38,
Line 14, after "the" insert -- subunits --;

Signed and Sealed this

Seventh Day of January, 2003

JAMES E. ROGAN
*Director of the United States Patent and Trademark Office*